(12) United States Patent
Shah

(10) Patent No.: US 12,285,485 B2
(45) Date of Patent: *Apr. 29, 2025

(54) METHODS OF TREATING PAIN

(71) Applicant: Semnur Pharmaceuticals, Inc., Palo Alto, CA (US)

(72) Inventor: Mahendra G. Shah, Mountain View, CA (US)

(73) Assignee: Semnur Pharmaceuticals, Inc., Palo Alto, CA (US)

( * ) Notice: Subject to any disclaimer, the term of this patent is extended or adjusted under 35 U.S.C. 154(b) by 258 days.

This patent is subject to a terminal disclaimer.

(21) Appl. No.: 17/244,348

(22) Filed: Apr. 29, 2021

(65) Prior Publication Data

US 2021/0386859 A1 Dec. 16, 2021

Related U.S. Application Data

(63) Continuation of application No. 16/667,297, filed on Oct. 29, 2019, now Pat. No. 11,020,485, which is a continuation of application No. 15/545,204, filed as application No. PCT/US2016/014165 on Jan. 20, 2016, now Pat. No. 10,500,284.

(60) Provisional application No. 62/106,045, filed on Jan. 21, 2015.

(51) Int. Cl.
| | |
|---|---|
| *A61K 47/36* | (2006.01) |
| *A61K 9/00* | (2006.01) |
| *A61K 9/08* | (2006.01) |
| *A61K 31/573* | (2006.01) |
| *A61K 31/661* | (2006.01) |
| *A61K 45/06* | (2006.01) |
| *A61K 47/02* | (2006.01) |

(52) U.S. Cl.
CPC ............ *A61K 47/36* (2013.01); *A61K 9/0019* (2013.01); *A61K 9/0085* (2013.01); *A61K 9/08* (2013.01); *A61K 31/573* (2013.01); *A61K 31/661* (2013.01); *A61K 45/06* (2013.01); *A61K 47/02* (2013.01)

(58) Field of Classification Search
CPC ........ A61K 47/36; A61K 9/0019; A61K 9/08; A61K 31/573; A61K 31/661
See application file for complete search history.

(56) References Cited

U.S. PATENT DOCUMENTS

| | | |
|---|---|---|
| 3,962,430 A | 6/1976 | O'Neill |
| 4,304,765 A | 12/1981 | Shell et al. |
| 5,106,615 A | 4/1992 | Dikstein |
| 6,251,876 B1 | 6/2001 | Bellini et al. |
| 6,747,090 B2 | 6/2004 | De Groot |
| 8,846,094 B2 | 9/2014 | Lyons et al. |
| 9,089,478 B2 | 7/2015 | Whitcup et al. |
| 9,833,460 B2 | 12/2017 | Shah |
| 10,117,938 B2 | 11/2018 | Shah |
| 10,500,284 B2 | 12/2019 | Shah |
| 10,744,144 B2 | 8/2020 | Shah |
| 11,020,485 B2 | 6/2021 | Shah |
| 11,364,251 B2 | 6/2022 | Shah |
| 12,016,867 B2 | 6/2024 | Shah |
| 2004/0006052 A1 | 1/2004 | Gudas et al. |
| 2005/0095235 A1 | 5/2005 | Austin et al. |
| 2005/0186229 A1 | 8/2005 | Clemente et al. |
| 2007/0020325 A1 | 1/2007 | Kuribayashi et al. |
| 2007/0099882 A1 | 5/2007 | Gurney et al. |
| 2007/0141160 A1 | 6/2007 | Brown et al. |
| 2007/0203095 A1 | 8/2007 | Sadozai et al. |
| 2009/0062720 A1 | 3/2009 | Anderson et al. |
| 2011/0281834 A1 | 11/2011 | Friden |
| 2013/0136780 A1 | 6/2013 | Tezel et al. |
| 2013/0142837 A1 | 6/2013 | Torrella et al. |
| 2021/0052605 A1 | 2/2021 | Shah |
| 2022/0370476 A1 | 11/2022 | Shah |

FOREIGN PATENT DOCUMENTS

| | | |
|---|---|---|
| CN | 1843333 A | 10/2006 |
| CN | 101918002 A | 12/2010 |
| EP | 0244178 A2 | 11/1987 |
| EP | 2067442 A1 | 6/2009 |
| GB | 1090492 A | 11/1967 |
| JP | 11-279065 A | 10/1999 |
| JP | 2007001926 A | 1/2007 |
| RU | 2459615 C1 | 8/2012 |
| WO | WO-1997/025025 A1 | 7/1997 |
| WO | WO-2008/157057 A2 | 12/2008 |
| WO | WO-2009/129148 A2 | 10/2009 |
| WO | WO-2009/129148 A3 | 10/2009 |
| WO | WO-2009/139924 A2 | 11/2009 |
| WO | WO-2009/139924 A3 | 11/2009 |
| WO | WO-2012/019009 A1 | 2/2012 |
| WO | WO-2013/096857 A1 | 6/2013 |

(Continued)

OTHER PUBLICATIONS

European Patent Office, Extended European Search Report for EP21173943.8, Nov. 11, 2021, 6 pages.
Barry, "Hyaluronic Acid Equivalent to Sham Injections in Patients with Knee DJD," American Family Physician 93(8):704 (2016).
Database WPI, Week 200004, Thomson Scientific, London, GB;AN 2000-041984 & JP H11 279065 A (Shiseido Co Ltd) Oct. 12, 1999 (Oct. 12, 1999), 1 page.
Dollo, G. et al., "Prolongation of Epidural Bupivacaine Effects with Hyaluronic Acid in Rabbits," Intl. J. Pharmaceutics, 272:109-119 (2004).
Ex Parte Quayle Office Action mailed on May 20, 2019, for U.S. Appl. No. 15/545,204, filed Jul. 20, 2017, 5 pages.

(Continued)

*Primary Examiner* — Barbara P Badio
(74) *Attorney, Agent, or Firm* — Fortem IP LLP

(57) ABSTRACT

Disclosed are aqueous pharmaceutical compositions which provide sustained released delivery of corticosteroid compounds. The pharmaceutical composition comprises a soluble corticosteroid and at least one viscosity enhancing agent. Also provided are methods for using the pharmaceutical compositions in an epidural injection, intra-articular injection, or an intra-lesional injection.

29 Claims, 25 Drawing Sheets

(56) References Cited

FOREIGN PATENT DOCUMENTS

WO  WO-2014/116876 A1  7/2014
WO  WO-2016/118649 A1  7/2016

OTHER PUBLICATIONS

Fernandez-Palazzi, F. et al. (1997). "Intraarticular Dexamethasone in Advanced Chronic Synovitis in Hemophilia," Clinical Orthopaedics and Related Research 343:25-29.
Final Office Action mailed on Aug. 1, 2016, for U.S. Appl. No. 14/162,625, filed Jan. 23, 2014, 9 pages.
Gazelka, H.M. et al. (2012). "Determination of the Particulate Size and Aggregation of Clonidine and Corticosteroids for Epidural Steroid Injection," Pain Physician 15:87-93.
Grecomoro, et al., "Therapeutic synergism between hyaluronic acid and dexamethasone in the intra-articular treatment of osteoarthritis of the knee: a preliminary open study," Current Medical Research and Opinion 13(1):49-55 (1992).
International Preliminary Report on Patentability mailed Jul. 25, 2017, by the International Searching Authority for Application No. PCT/US2016/014165, filed Jan. 20, 2016, 10 pages.
International Search Report and Written Opinion mailed May 2, 2016, by the International Searching Authority for Application No. PCT/US2016/014165, filed Jan. 20, 2016, 14 pages.
International Search Report and Written Opinion mailed on Apr. 16, 2014, for PCT Patent Application No. PCT/US2014/012824, filed on Jan. 23, 2014, 19 pages.
Klingenberg, "Hyaluronic Acid—Creation of Slow-release Formulations for Osteoarthritis Treatments" Clinical & Medical Research International Pharmaceutical Industry 5(4):48-53 (2013).
MacMahon, P.J. et al. (2009). "Injectable corticosteroid and local anesthetic preparations: a review for radiologists," Radiology 252(3):647-661.
Mehta, D.P. et al. (2007). "Sodium hyaluronate of defined molecular size for treating osteoarthritis," Current Science 92(2):209-213.
Neustadt, D.H. (2006). "Intra-Articular Injections for Osteoarthritis of the Knee," Cleveland Clinic Journal of Medicine 73(10):897-911.
Non-Final Office Action issued by The United States Patent and Trademark Office for U.S. Appl. No. 15/545,204, dated Oct. 2, 2018, 9 pages.
Non-Final Office Action issued by The United States Patent and Trademark Office for U.S. Appl. No. 15/798,053, dated Jun. 15, 2018, 6 pages.
Non-Final Office Action mailed on Feb. 2, 2016, for U.S. Appl. No. 14/162,625, filed Jan. 23, 2014, 7 pages.
Non-Final Office Action mailed on Mar. 9, 2017, for U.S. Appl. No. 14/162,625, filed Jan. 23, 2014, 9 pages.
Notice of Allowance issued by The United States Patent and Trademark Office for U.S. Appl. No. 15/907,057, dated Aug. 24, 2018, 8 pages.
Notice of Allowance mailed on Jul. 31, 2017, for U.S. Appl. No. 14/162,625, filed Jan. 23, 2014, 7 pages.
Notice of Allowance mailed on Dec. 26, 2018, for U.S. Appl. No. 15/798,053, filed Oct. 30, 2017, 8 pages.
Notice of Allowance mailed on Jul. 31, 2019, for U.S. Appl. No. 15/545,204, filed Jul. 20, 2017, 10 pages.
Non-Final Office Action issued by The United States Patent and Trademark Office for U.S. Appl. No. 15/907,057, dated May 10, 2018, 8 pages.
Paul, S. et al. (1999). "Pressure Measurements During Injection of Corticosteroids: In Vivo Studies," *Medical and Biological Engineering and Computing* 37:645-651.
Supplemental Notice of Allowability issued by The United States Patent and Trademark Office for U.S. Appl. No. 15/798,053, dated Jan. 14, 2019, 3 pages.
Notice of Allowance issued by The United States Patent and Trademark Office for U.S. Appl. No. 15/798,053, dated Apr. 3, 2020, 8 pages.
Non-Final Office Action mailed Sep. 11, 2020 by The United States Patent and Trademark Office for U.S. Appl. No. 16/667,297, filed Oct. 29, 2019, 5 pages.
Notice of Allowance mailed Jan. 25, 2021 by The United States Patent and Trademark Office for U.S. Appl. No. 16/667,297, filed Oct. 29, 2019, 5 pages.
Non-Final Office Action mailed Jul. 8, 2021 by The United States Patent and Trademark Office for U.S. Appl. No. 16/921,628, filed Jul. 6, 2020, 6 pages.

METHODS OF TREATING PAIN

CROSS-REFERENCE TO RELATED APPLICATIONS

This application is a continuation of U.S. patent application Ser. No. 16/667,297, filed on Oct. 29, 2019, now issued U.S. Pat. No. 11,020,485, which is a continuation of U.S. patent application Ser. No. 15/545,204, filed on Jul. 20, 2017, now issued U.S. Pat. No. 10,500,284, which is a National Phase application under 35 U.S.C. § 371 of International Application No. PCT/US2016/014165, filed on Jan. 20, 2016, which designated the United States, and claims priority to U.S. Provisional Patent Application No. 62/106,045, filed on Jan. 21, 2015, the disclosures of which are hereby incorporated herein by reference in their entireties entirety.

FIELD OF INVENTION

The present application relates to a pharmaceutical composition comprising a soluble corticosteroid and a viscosity enhancing agent. The pharmaceutical composition is suitable for local administration such as epidural injection, intra-articular injection, or intra-lesional injection.

BACKGROUND OF THE INVENTION

In the spine, the epidural space (also known as "extradural space" or "peridural space") is the outermost part of the spinal canal. It is the space within the canal (formed by the surrounding vertebrae) lying outside the dura mater (which encloses the arachnoid mater, subarachnoid space, the cerebrospinal fluid, and the spinal cord). In humans, the epidural space contains lymphatics, spinal nerve roots, loose fatty tissue, small arteries, and a network of large, thin-walled blood vessels called the epidural venous plexus.

An epidural steroid injection is a minimally invasive procedure that can help relieve neck, arm, back, and leg pain in an individual caused by inflamed spinal nerves. For instance, an epidural steroid injection may be performed to relieve pain caused by spinal stenosis, spondylolysis, or disc herniation in an individual. Medicines are delivered to the spinal nerve through the epidural space, the area between the protective covering (dura) of the spinal cord and vertebrae. Corticosteroid injections can reduce inflammation and can be effective when delivered directly into the painful area of the individual.

The goal of an epidural steroid injection is to place the medication near the area of injury and/or pathology within the spine. Interlaminar, caudal, and transforaminal injections are typically used for epidural steroid injections. An interlaminar epidural injection is performed by placing a needle between the bony vertebrae in the epidural space, followed by injection of medicine. A caudal injection is an injection into the lowest portion of the epidural space, into the area between the membrane that contains the spinal fluid and the thickest ligament between vertebrae. A transforaminal injection is an injection into the opening (also known as a foramen) at the side of the spine where a nerve roots exits.

Prednisolone is a corticosteroid drug with predominant glucocorticoid and low mineralocorticoid activity, making it useful for the treatment of a wide range of inflammatory and auto-immune conditions such as asthma, uveitis, pyoderma gangrenosum, rheumatoid arthritis, ulcerative colitis, temporal arteritis and Crohn's disease, Bell's palsy, multiple sclerosis, cluster headaches, vasculitis, acute lymphoblastic leukemia and autoimmune hepatitis, systemic lupus erythematosus, Kawasaki disease and dermatomyositis.

Methylprednisolone is typically used for its anti-inflammatory effects. The list of medical conditions for which methylprednisolone is prescribed is rather long, and is similar to other corticosteroids such as prednisolone. Common uses include arthritis therapy and short-term treatment of bronchial inflammation or acute bronchitis due to various respiratory diseases. It is used both in the treatment of acute periods and long-term management of autoimmune diseases, most notably systemic lupus erythematosus. It is also used as a treatment for multiple sclerosis.

Dexamethasone is a potent synthetic member of the glucocorticoid class of steroid drugs. It acts as an anti-inflammatory and immunosuppressant. Dexamethasone is used to treat many inflammatory and autoimmune conditions, such as rheumatoid arthritis and bronchospasm. Dexamethasone may also be used to treat idiopathic thrombocytopenic purpura, which is a decreased number of platelets due to an immune problem.

Triamcinolone acetonide is a synthetic corticosteroid with marked anti-inflammatory action. KENALOG®-10 Injection (triamcinolone acetonide injectable suspension, USP) is triamcinolone acetonide, in a sterile aqueous suspension suitable for intralesional and intra-articular injection, and not suitable for intravenous, intramuscular, intraocular, epidural, or intrathecal use. Each mL of the sterile aqueous suspension provides 10 mg triamcinolone acetonide, with sodium chloride for isotonicity, 0.9% (w/v) benzyl alcohol as preservative, 0.75% carboxymethylcellulose sodium, and 0.04% polysorbate 80; sodium hydroxide or hydrochloric acid may have been added to adjust pH between 5.0 and 7.5.

Existing pharmaceutical compositions may have immediate or short-term effects on alleviating pain. This may be sufficient for purposes of short-term administration such as to overcome an acute episode or exacerbation of pain. However, such formulations may require repeated administration, especially for sustained or chronic pain. In addition, for localized pain, epidural injections that result in the diffusion of the active ingredient outside of the target area may be undesirable and may increase the need for an overall higher dose to ensure that the target area is exposed to an effective dose. Furthermore, pharmaceutical compositions and methods of administration that contribute to unintended placement of the composition can lead to undesirable effects such as arachnoiditis caused from an epidural injection.

There exists a need for an improved pharmaceutical composition that can provide a quick local onset of action as well as a long lasting effect; have physical characteristics that facilitate injection into various parts of the body; and be shelf-stable. In particular, a stable, long-acting pharmaceutical composition suited for epidural, intra-articular, or intralesional injection is desirable.

One solution to this need was put forth in the form of a pharmaceutical composition comprising both a soluble form and an insoluble form of a corticosteroid in water (PCT International Publication No. WO 2014/116876). The soluble form of the corticosteroid offers immediate relief, whereas the insoluble form provides a longer-lasting effect. However, in 2014, the U.S. Food and Drug Administration (FDA) issued a warning that injection of corticosteroids into the epidural space of the spine may result in rare but serious adverse effects such as loss of vision, stroke, paralysis, and death. In response, 17 safety recommendations proposed by the Multi-Society Pain Workgroup (MPW) were approved, including the recommendation that particulate steroids should not be used in transforaminal injections. Transforaminal injections are attractive routes for administration of pain medication because the injection site location is closest to the presumed site of inflammation. Accordingly, there exists a need for improved pharmaceutical compositions that can provide both quick onset of action and a long lasting effect, and are approved for all three routes of injection (transforaminal, interlaminar, and caudal).

SUMMARY OF THE INVENTION

In one aspect, the application discloses an aqueous pharmaceutical composition comprising a soluble corticosteroid and at least one viscosity enhancing agent, wherein the pharmaceutical composition has a viscosity of between 1 kcP and 200 kcP.

In one embodiment, the application discloses an aqueous pharmaceutical composition, wherein the soluble corticosteroid is selected from salts and esters of the group consisting of dexamethasone, methylprednisolone, prednisolone, and triamcinolone acetonide. In another embodiment, the soluble corticosteroid is selected from the group consisting of dexamethasone sodium phosphate, methylprednisolone sodium succinate, prednisolone sodium succinate, and triamcinolone acetonide phosphate ester. In yet another embodiment, the soluble corticosteroid is dexamethasone sodium phosphate.

In one embodiment, at least one viscosity enhancing agent is selected from the group consisting of sodium hyaluronate, hyaluronic acid, cross-linked hyaluronic acid, polyvinylpyrrolidone, hydroxypropyl methylcellulose, hydroxypropyl cellulose, hydroxyethyl cellulose, and glycerol. In another embodiment, at least one viscosity enhancing agent is sodium hyaluronate.

In some embodiments, the soluble corticosteroid is dexamethasone sodium phosphate and at least one viscosity enhancing agent is sodium hyaluronate. In some embodiments, the aqueous pharmaceutical composition comprises less than 2% w/v of the viscosity enhancing agent. In still other embodiments, the aqueous pharmaceutical composition further comprises a preservative and/or an anesthetic.

In another aspect, the application provides a method for treating inflammation and/or pain in an individual in need thereof, comprising injecting into an individual an aqueous pharmaceutical composition disclosed herein. In one embodiment, the pharmaceutical composition is injected into the epidural space. In a further embodiment, less than 20 N of force is used to inject the pharmaceutical composition into the epidural space at a rate of about 0.5"/min. In yet another embodiment, the individual is injected with the formulation once every 1 to 12 weeks. In one embodiment, the soluble corticosteroid is selected from salts and esters of the group consisting of dexamethasone, methylprednisolone, prednisolone, and triamcinolone acetonide. In another embodiment, the soluble corticosteroid is selected from the group consisting of dexamethasone sodium phosphate, methylprednisolone sodium succinate, prednisolone sodium succinate, and triamcinolone acetonide phosphate ester. In yet another embodiment, the soluble corticosteroid is dexamethasone sodium phosphate. In one embodiment, at least one viscosity enhancing agent is selected from the group consisting of sodium hyaluronate, hyaluronic acid, cross-linked hyaluronic acid, polyvinylpyrrolidone, hydroxypropyl methylcellulose, hydroxypropyl cellulose, hydroxyethyl cellulose, and glycerol. In another embodiment, at least one viscosity enhancing agent is sodium hyaluronate. In some embodiments, the soluble corticosteroid is dexamethasone sodium phosphate and at least one viscosity enhancing agent is sodium hyaluronate. In some embodiments, the formulation comprises less than 2% w/v of the viscosity enhancing agent. In yet other embodiments, the formulation further comprises a preservative and/or an anesthetic.

In yet another aspect, the application provides a syringe comprising an aqueous pharmaceutical composition disclosed herein.

DETAILED DESCRIPTION OF THE INVENTION

Figure 1:
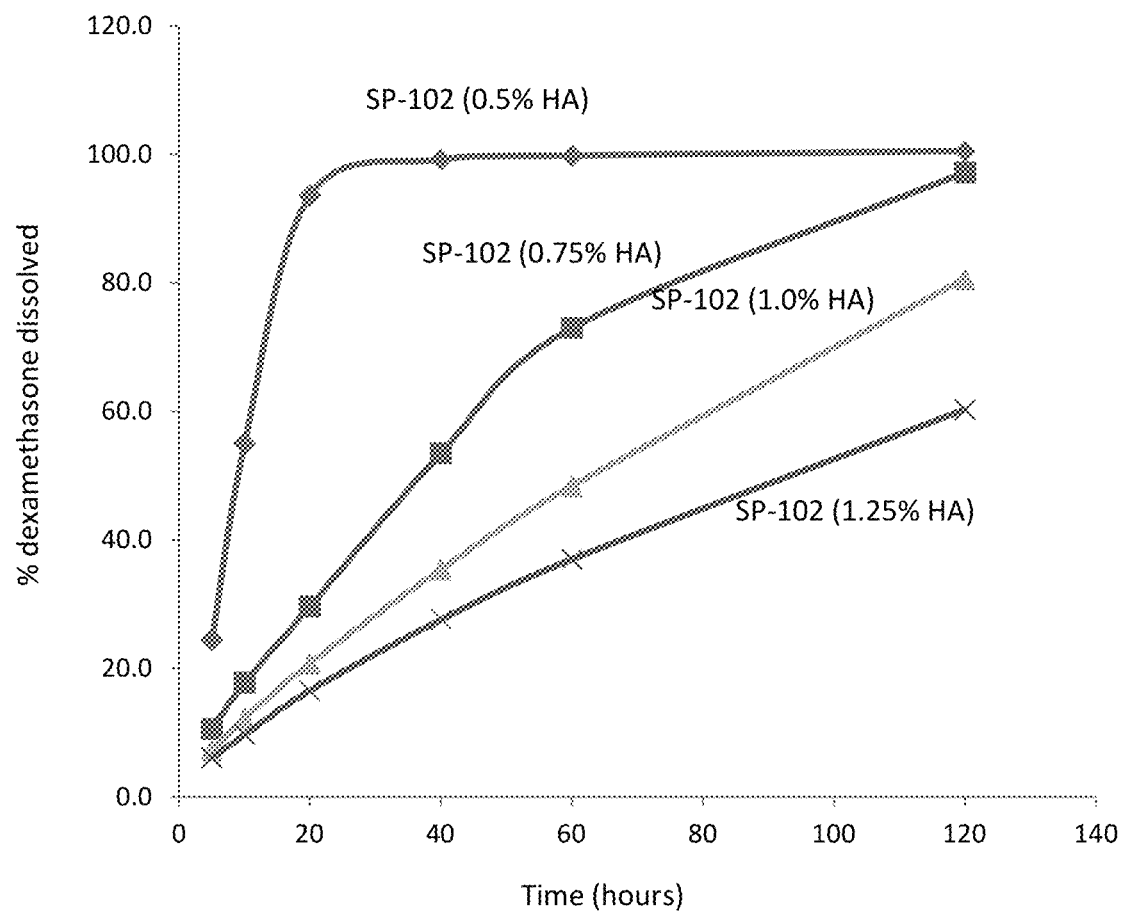
FIG. 1 shows the dissolution profile of SP-102 formulations in phosphate buffer, (0.05 M, pH 7) and 0.5% Tween 80.

The present application is directed to a pharmaceutical composition comprising a soluble corticosteroid and a viscosity enhancing agent. The pharmaceutical composition is suitable for local administration such as epidural injection, intra-articular injection, or intra-lesional injection. Suitable corticosteroids for the present application include salts or esters of the following: methylprednisolone, dexamethasone, prednisolone, and triamcinolone acetonide.

The inventor has discovered the advantages of combining a soluble form of a corticosteroid with a viscosity enhancing agent in a pharmaceutical composition for a local injection. The viscosity enhancing agent significantly prolongs the duration of direct corticosteroid exposure at the injection site. The viscosity enhancing agent also provides for slow release of the steroid. The released steroid provides onset of action on a target site such as inflamed nerves and tissues in a sustained and/or prolonged manner. The longer lasting effect may allow a steroid to be injected periodically instead of daily, which is difficult to do via epidural or intra-articular administration.

Mixtures of soluble steroids and viscosity enhancing agents have previously been described for intraocular administration (EP0244178). However, the viscosity of ophthalmological preparations is typically 25-50 cps. In order to achieve a sufficiently long-lasting effect of a soluble steroid administered by epidural injection, the viscosity of the injection solution must be much higher (minimum of 2000-3000 cps). Highly viscous solutions, however, can be difficult to inject without undue force. For example, mixtures of the anesthetic drug bupivacaine with 1% (w/w) hyaluronic acid could not be administered through an epidural needle or catheter (Dollo, G. et al. *Intl. J. Pharmaceutics*, 2004, 272, 109-119). The present invention provides for mixtures of soluble steroids and viscosity enhancing agents that have desirable characteristics of syringeability and injectability for local administration such as epidural injection, intra-articular injection, or intra-lesional injection.

Formulation Components

Soluble corticosteroids. Non-limiting examples of soluble corticosteroids include salts or esters of the following: dexamethasone, methylprednisolone, prednisolone, and triamcinolone acetonide. The soluble corticosteroid may possess a range of solubilities, but it is sufficiently soluble to be dissolved in the pharmaceutical formulation. The solubility of the corticosteroid is determined in part by its chemical form, such as salts or esters. Soluble forms of corticosteroids include salts thereof, such as sodium, phosphate, succinate, and combinations thereof.

Non-limiting examples of soluble corticosteroids include dexamethasone sodium phosphate, methylprednisolone sodium succinate, prednisolone sodium succinate, and triamcinolone acetonide phosphate ester.

It is understood that the soluble corticosteroid can provide both a quick and a sustained effect, by virtue of release from the viscosity enhancing agent, after administration to the individual. In some embodiments, injection of the soluble corticosteroid into an individual, provides a pharmacodynamic action of corticosteroid for at least about 1, about 2, about 3, about 4, about 5, about 6, about 7, about 8, about 9, about 10, about 11, or about 12 weeks. In some embodiments, the pharmacodynamic action of the corticosteroid provides an amount effective to reduce or inhibit inflammation and/or pain. In some embodiments, the pharmacodynamic action of the corticosteroid provides an amount effective to inhibit inflammation and/or pain for up to 8 weeks. In some embodiments, the pharmacodynamic action of the corticosteroid provides an amount effective to reduce inflammation and/or pain for up to 12 weeks.

It is understood that the pharmaceutical compositions described herein are substantially free of insoluble corticosteroids. In some embodiments, the pharmaceutical compositions are completely free of insoluble corticosteroids.

Viscosity enhancing agent. A viscosity enhancing agent is included in the pharmaceutical composition. The viscosity enhancing agent provides an advantage that when the pharmaceutical composition is administered into a target site (e.g., the epidural space of an individual), the formulation stays longer in the target site due to a low degree of circulation of the viscous formulation in the target site. The viscosity enhancing agent may also promote the binding of the active drug to a target site and to enhance drug absorption and bioavailability locally.

The viscosity of the composition also contributes to the stability of the pharmaceutical composition. Higher viscosities may improve shelf-life. The viscosity of the composition is, in large part, influenced by the amount of the viscosity enhancing agent. Higher concentrations of the viscosity enhancing agent compared to lower concentrations results in a higher viscosity. Temperature also affects viscosity, with lower temperatures resulting in higher viscosities compared to higher temperatures of the same composition.

Suitable viscosity enhancing agent include sodium hyaluronate, hyaluronic acid, polyvinylpyrrolidone (PVP), cross-linked hyaluronic acid, hydroxypropyl methylcellulose, hydroxypropyl cellulose, hydroxylethyl cellulose, glycerol, or a mixture thereof. Preferred viscosity enhancing agents include sodium hyaluronate, polyvinylpyrrolidone (PVP), sodium hydroxypropyl cellulose, and carboxy methylcellulose. The present formulation does not include polyethylene glycol due to potential side effects.

The amount of the viscosity enhancing agent is based on the agent used, and is in general in an amount of about 0.05-30% (w/v). In some embodiments, the concentration of the viscosity enhancing agent is about 0.1% w/v, about 0.25% w/v, about 0.5% w/v, about 0.75% w/v, about 1.0% w/v, about 1.1% w/v, about 1.15% w/v, about 1.20% w/v, about 1.25% w/v, about 1.30% w/v, about 1.35% w/v, about 1.40% w/v, about 1.45% w/v, or about 1.5% w/v.

In some embodiments, the concentration of the viscosity enhancing agent is between 0.05% w/v and 1.5% w/v; 0.05% w/v and 0.5% w/v; 0.1% w/v and 3.0% w/v; 0.1% w/v and 1.5% w/v; 0.1% w/v and 1.0% w/v; 0.5% w/v and 1% w/v; 0.5% w/v and 2.5% w/v; 1.0% w/v and 3.0% w/v; 1.0% w/v and 1.5% w/v; 1.0% w/v and 1.25% w/v; 1.25% w/v and 1.5% w/v; or 1.5% w/v and 3.0% w/v.

In some embodiments, the molecular weight of the viscosity enhancing agent is between 500 kDa and 5.0 MDa; 500 kDa and 3.0 MDa; 500 kDa and 2.0 MDa; 500 kDa and 1.0 MDa; 500 kDa and 2.0 MDa; 1.0 MDa and 3.0 MDa; 1.0 MDa and 2.5 MDa; 1.0 MDa and 2.0 MDa; and 1.2 MDa and 1.8 MDa. In some embodiments, the molecular weights of sodium hyaluronate is about 711 kDa; about 880 kDa; about 1.56 MDa; about 1.8 MDa and about 2.65 MDa. In some of the embodiments, the molecular weight is the number average molecular weight, and in other embodiments the molecular weight is the weight average molecular weight. In some of the foregoing embodiments, the viscosity enhancing agent is sodium hyaluronate. In some embodiments, the viscosity enhancing agent is hyaluronic acid or a pharmaceutically acceptable salt of hyaluronate, such as sodium salt, phosphate salt or calcium salt.

In some embodiments, the viscosity of the pharmaceutical composition is about 300 kcP, about 250 kcP, about 200 kcP, about 150 kcP, about 140 kcP, about 130 kcP, about 120 kcP, about 110 kcP, about 100 kcP, about 90 kcP, about 80 kcP, about, 70 kcP, about 40 kcP, about, 30 kcP, about 25 kcP, about 20 kcP, about 15 kcP, about 10 kcP, about 5 kcP, about 4 kcP, about 3 kcP, about 2 kcP, or about 1 kcP.

In some embodiments, the viscosity of the composition is between 1 kcP and 300 kcP; 1 kcP and 100 kcP; 1 kcP and 50 kcP; 1 kcP and 10 kcP; 10 kcP and 50 kcP; 10 kcP and 100 kcP; 50 kcP and 100 kcP; 100 kcP and 300 kcP; 50 kcP and 200 kcP; 75 kcP and 180 kcP; 100 kcP and 150 kcP; 150 kcP and 200 kcP; 200 kcP and 250 kcP; 250 kcP and 300 kcP.

In some embodiments, the pharmaceutical composition is a gel. In alternative embodiments, the pharmaceutical composition is an aqueous solution.

Buffer. Suitable buffering agents for use with the pharmaceutical compositions disclosed herein include, but are not limited to, organic acid salts such as salts of citric acid, ascorbic acid, gluconic acid, carbonic acid, tartaric acid, succinic acid, acetic acid or phthalic acid; Tris, thomethamine hydrochloride, or phosphate buffer. In some embodiments, the buffer is physiologically compatible.

pH. The pH of the formulation may be inherently provided by the excipients present in the formulation; alternatively, a pH adjustment agent may be employed. A pH adjustment agent such as a buffer or a simple acid or base can be added to the pharmaceutical composition to maintain the pH to 6-8. For example, the amount of a pH adjusting agent is in general 0.1-10%. In some embodiments, the pH of the formulation is within physiological range.

Osmolality. The osmolality of the formulation is between 200 mOsm/kg and 350 mOsm/kg, 250 mOsm/kg and 300 mOsm/kg, 280 mOsm/kg and 290 mOsm/kg. In some embodiments, the osmolality of the formulation is within a physiological range. In some embodiments, the pharmaceutical composition is isotonic in a human.

Anesthetic. In one embodiment, the pharmaceutical composition further comprises an anesthetic agent such as lidocaine, bupivacaine, or benzocaine.

Surfactant. The present formulation preferably does not include a surfactant. However, in some embodiments, the pharmaceutical composition comprises one or more non-ionic surfactants. Inclusion of a surfactant increases the solubility and wettability of the drug particles. Suitable non-ionic surfactants include polysorbates (e.g., TWEEN®-80, TWEEN®-20), tyloxapol, polyoxyl castor oil, polaxamers, polyethylene glycol, caprylic triglyceride, polyoxyl stearates (e.g., oxyethylene monostearate), polyoxyethylated vegetable oils and glyceryl monostearate. A preferred non-ionic surfactant is a polysorbate such as TWEEN®-80. The amount of the non-ionic surfactant in the pharmaceutical composition, if present, is in general 0.001-10, or 0.01-1% (w/v) of the pharmaceutical composition.

Shelf life. The term "shelf life" refers to the amount of time the pharmaceutical composition may be stored without loss of potency and/or performance profile. In some embodiments, shelf life refers to the amount of time the pharmaceutical composition may be stored without a loss of more than 2%, 5%, 8% or 10% of the potency and/or performance. The preservative-free pharmaceutical compositions provided herein are designed to have shelf life of at least 12, 24 or 36 months. In some embodiments, the pharmaceutical compositions have a shelf life of between 12 and 24 months. In some embodiments, the pharmaceutical composition is stored at room temperature and is shelf stable for at least 12, 24 or 36 months. In some embodiments, the pharmaceutical composition is stored below room temperature and has a shelf life of at least 12, 24, or 36 months.

Preservatives. The present formulation preferably does not include a preservative. However, in some embodiments, the pharmaceutical composition comprises one or more preservatives. Inclusion of a preservative, such as an antimicrobial preservative, increases the shelf-life of the pharmaceutical composition. Any preservative which does not adversely interact with the active drug or any of the excipients may be employed. For example, preservatives include ethanol, benzyl alcohol, benzalkonium chloride, benzethonium chloride, benzoic acid, bronopol, butyl-paraben, cetrimide, chlorhexidine. The amount of preservative may range, for example, from about 0.01-1%.

Exemplary Formulations

In one embodiment, the aqueous pharmaceutical composition comprises a soluble corticosteroid and at least one viscosity enhancing agent, wherein the aqueous pharmaceutical composition has a viscosity of between 1 kcP and 200 kcP. In some embodiments, the aqueous pharmaceutical composition is in a unit dose and has a volume of 1 mL, 2 mL, 3 mL, 4 mL, 5 mL, 6 mL, 7 mL, 8 mL, or 10 mL. In some embodiments, the viscosity enhancing agent concentration is between 0.05% w/v and 1.5% w/v; 0.05% w/v and 0.5% w/v; 0.1% w/v and 1.5% w/v; 0.1% w/v and 1.0% w/v; 0.5% w/v and 1% w/v; 0.5% w/v and 2.5% w/v; 1.0% w/v and 1.5% w/v; 1.0% w/v and 1.25% w/v; or 1.25% w/v and 1.5% w/v.

In one embodiment, the pharmaceutical composition comprises soluble methylprednisolone sodium succinate and at least one viscosity enhancing agent in an aqueous solution such as water, wherein the pharmaceutical composition has a viscosity of between 1 kcP and 200 kcP. In some embodiments, the aqueous pharmaceutical composition is in a unit dose and has a volume of 1 mL, 2 mL, 3 mL, 4 mL, 5 mL, 6 mL, 7 mL, 8 mL, or 10 mL. In some embodiments, the viscosity enhancing agent concentration is between 0.05% w/v and 1.5% w/v; 0.05% w/v and 0.5% w/v; 0.1% w/v and 1.5% w/v; 0.1% w/v and 1.0% w/v; 0.5% w/v and 1% w/v; 0.5% w/v and 2.5% w/v; 1.0% w/v and 1.5% w/v; 1.0% w/v and 1.25% w/v; or 1.25% w/v and 1.5% w/v. In some embodiments, the dose per injection of methylprednisolone is in the range of 20 to 120 mg/dose in 1 to 10 ml of a sterile solution such as water for injection or saline.

In one embodiment, the pharmaceutical composition comprises soluble prednisolone sodium succinate and at least one viscosity enhancing agent in an aqueous solution such as water, wherein the pharmaceutical composition has a viscosity of between 1 kcP and 200 kcP. In some embodiments, the aqueous pharmaceutical composition is in a unit dose and has a volume of 1 mL, 2 mL, 3 mL, 4 mL, 5 mL, 6 mL, 7 mL, 8 mL, or 10 mL. In some embodiments, the viscosity enhancing agent concentration is between 0.05% w/v and 1.5% w/v; 0.05% w/v and 0.5% w/v; 0.1% w/v and 1.5% w/v; 0.1% w/v and 1.0% w/v; 0.5% w/v and 1% w/v; 0.5% w/v and 2.5% w/v; 1.0% w/v and 1.5% w/v; 1.0% w/v and 1.25% w/v; or 1.25% w/v and 1.5% w/v. In some embodiments, the dose per injection of prednisolone is in the range of 20 to 120 mg/dose in 1 to 10 ml of a sterile solution such as water for injection or saline.

In one embodiment, the pharmaceutical composition comprises soluble dexamethasone sodium phosphate and at least one viscosity enhancing agent in an aqueous solution such as water, wherein the pharmaceutical composition has a viscosity of between 1 kcP and 200 kcP. In some embodiments, the aqueous pharmaceutical composition is in a unit dose and has a volume of 1 mL, 2 mL, 3 mL, 4 mL, 5 mL, 6 mL, 7 mL, 8 mL, or 10 mL. In some embodiments, the viscosity enhancing agent concentration is between 0.05% w/v and 1.5% w/v; 0.05% w/v and 0.5% w/v; 0.1% w/v and 1.5% w/v; 0.1% w/v and 1.0% w/v; 0.5% w/v and 1% w/v;

0.5% w/v and 2.5% w/v; 1.0% w/v and 1.5% w/v; 1.0% w/v and 1.25% w/v; or 1.25% w/v and 1.5% w/v. The dose per injection of dexamethasone is in the range of 3 to 20 mg/dose in 1 to 10 ml of a sterile solution such as water for injection or saline.

Yet in another embodiment, the pharmaceutical composition comprises soluble triamcinolone acetonide phosphate ester and at least one viscosity enhancing agent in an aqueous solution such as water, wherein the pharmaceutical composition has a viscosity of between 1 kcP and 200 kcP. In some embodiments, the aqueous pharmaceutical composition is in a unit dose and has a volume of 1 mL, 2 mL, 3 mL, 4 mL, 5 mL, 6 mL, 7 mL, 8 mL, or 10 mL. In some embodiments, the viscosity enhancing agent concentration is between 0.05% w/v and 1.5% w/v; 0.05% w/v and 0.5% w/v; 0.1% w/v and 1.5% w/v; 0.1% w/v and 1.0% w/v; 0.5% w/v and 1% w/v; 0.5% w/v and 2.5% w/v; 1.0% w/v and 1.5% w/v; 1.0% w/v and 1.25% w/v; or 1.25% w/v and 1.5% w/v. The dose per injection of triamcinolone is in the range of 20 mg to 120 mg/dose in 1 to 10 ml of a sterile solution such as water for injection or saline.

In further embodiments, the aqueous pharmaceutical composition comprises soluble dexamethasone sodium phosphate and sodium hyaluronate, wherein the aqueous pharmaceutical composition has a viscosity of between 1 kcP and 200 kcP. In some embodiments, the molecular weight of sodium hyaluronate is 500 kDa and 2.0 MDa. In other embodiments, the molecular weight of sodium hyaluronate is 1.2 MDa and 1.8 MDa. In some embodiments, the sodium hyaluronate concentration is between 0.05% w/v and 1.5% w/v; 0.05% w/v and 0.5% w/v; 0.1% w/v and 1.5% w/v; 0.1% w/v and 1.0% w/v; 0.5% w/v and 1% w/v; 0.5% w/v and 2.5% w/v; 1.0% w/v and 1.5% w/v; 1.0% w/v and 1.25% w/v; or 1.25% w/v and 1.5% w/v. In some embodiments, the aqueous pharmaceutical composition is in a unit dose and has a volume of 1 mL, 2 mL, 3 mL, 4 mL, 5 mL, 6 mL, 7 mL, 8 mL, 9 mL, or 10 mL.

In further embodiments, the aqueous pharmaceutical composition comprises soluble dexamethasone sodium phosphate and hyaluronic acid, wherein the aqueous pharmaceutical composition has a viscosity of between 1 kcP and 200 kcP. In some embodiments, the molecular weight of hyaluronic acid is 500 kDa and 2.0 MDa. In other embodiments, the molecular weight of hyaluronic acid is 1.2 MDa and 1.8 MDa. In some embodiments, the hyaluronic acid concentration is between 0.05% w/v and 1.5% w/v; 0.05% w/v and 0.5% w/v; 0.1% w/v and 1.5% w/v; 0.1% w/v and 1.0% w/v; 0.5% w/v and 1% w/v; 0.5% w/v and 2.5% w/v; 1.0% w/v and 1.5% w/v; 1.0% w/v and 1.25% w/v; or 1.25% w/v and 1.5% w/v. In some embodiments, the aqueous pharmaceutical composition is in a unit dose and has a volume of 1 mL, 2 mL, 3 mL, 4 mL, 5 mL, 6 mL, 7 mL, 8 mL, 9 mL, or 10 mL.

Each of the exemplary formulations in Table 1 comprises soluble dexamethasone sodium phosphate at a weight equivalent to 5 mg/mL of dexamethasone and varying amounts of sodium hyaluronate. The molecular weight of the sodium hyaluronate is 1.56 MDa. The formulations further comprise a physiologically compatible buffer solution, such as 15 mM PBS solution. Each of the formulations are prepared in a 1 mL, 2 mL, 3 mL, 4 mL, 5 mL, 6 mL, 7 mL, 8 mL, 9 mL, and 10 mL unit doses.

TABLE 1

Exemplary formulations of soluble dexamethasone phosphate and hyaluronic acid.

| # | Sodium Hyaluronate, 1.56 MDa (% w/v) | Dexamethasone Sodium Phosphate (mg/mL) |
|---|---|---|
| 1 | 0.05 | 6.58 |
| 2 | 0.055 | 6.58 |
| 3 | 0.06 | 6.58 |
| 4 | 0.065 | 6.58 |
| 5 | 0.07 | 6.58 |
| 6 | 0.075 | 6.58 |
| 7 | 0.08 | 6.58 |
| 8 | 0.085 | 6.58 |
| 9 | 0.09 | 6.58 |
| 10 | 0.095 | 6.58 |
| 11 | 0.10 | 6.58 |
| 12 | 0.15 | 6.58 |
| 13 | 0.20 | 6.58 |
| 14 | 0.25 | 6.58 |
| 15 | 0.30 | 6.58 |
| 16 | 0.35 | 6.58 |
| 17 | 0.40 | 6.58 |
| 18 | 0.45 | 6.58 |
| 19 | 0.50 | 6.58 |
| 20 | 0.55 | 6.58 |
| 21 | 0.60 | 6.58 |
| 22 | 0.65 | 6.58 |
| 23 | 0.70 | 6.58 |
| 24 | 0.75 | 6.58 |
| 25 | 0.80 | 6.58 |
| 26 | 0.85 | 6.58 |
| 27 | 0.90 | 6.58 |
| 28 | 0.95 | 6.58 |
| 29 | 1.0 | 6.58 |
| 30 | 1.05 | 6.58 |
| 31 | 1.1 | 6.58 |
| 32 | 1.15 | 6.58 |
| 33 | 1.2 | 6.58 |
| 34 | 1.25 | 6.58 |
| 35 | 1.3 | 6.58 |
| 36 | 1.35 | 6.58 |
| 37 | 1.4 | 6.58 |
| 38 | 1.45 | 6.58 |
| 39 | 1.5 | 6.58 |

Each of the formulations listed in Table 1 further optionally contain an anesthetic and/or preservative. In some embodiments, the soluble corticosteroids of each of the formulations disclosed in Table 1 can be replaced with corticosteroids selected from the group consisting of methylprednisolone sodium succinate, prednisolone sodium succinate, and triamcinolone acetonide phosphate ester.

Packaging and kits. The present formulation can be packaged in a unit dose vial or syringe. It can also be packaged in a two-compartment vial or syringe with the soluble steroid and viscosity enhancing agent each in a separate compartment. In some embodiments, the unit dose is between 1 mL and 10 mL; 2 mL and 8 mL; and 2 mL and 5 mL. In some embodiments, the unit dose is about 1 mL, about 2 mL, about 2.5 mL, about 3 mL, about 3.5 mL, about 4 mL, about 4.5 mL, about 5 mL, or about 5.5 mL. In any of the foregoing embodiments, the unit dose is a gel pharmaceutical composition. In other foregoing embodiments, the unit dose is an aqueous pharmaceutical composition. The present disclosure also provides for a kit comprising a pharmaceutical formulation disclosed herein and instructions for use.

In some of the foregoing embodiments, the pharmaceutical composition is aseptic. In some of the foregoing embodiments, the pharmaceutical composition is prepared using aseptic techniques. For instance, the various components of the composition may be individually sterilized and then combined under aseptic conditions to provide the sterile pharmaceutical composition. In some of the foregoing embodiments, the pharmaceutical composition is terminally sterilized.

Methods

The present application also provides methods for treating inflammation and/or pain such as those associated with rheumatoid arthritis, osteoarthritis, lower back pain, tendonitis, spinal stenosis, disc herniation, radiculitis and chronic discogenic pain with any of the aqueous pharmaceutical compositions disclosed herein.

In one embodiment, the method comprises the steps of identifying an individual suffering from inflammation and/or pain, and injecting to the epidural space of the individual any of the aqueous pharmaceutical compositions disclosed herein. The method optionally comprises a step of injecting to the epidural space of the individual an anesthetic agent such as lidocaine, bupivacaine, or benzocaine. The anesthetic agent can be administered in a separate injection or can be combined with the aqueous pharmaceutical composition and injected together.

In another embodiment, the method comprises the steps of identifying an individual suffering from inflammation and/or pain, and injecting to a skin lesion of the individual any of the aqueous pharmaceutical compositions disclosed herein. The method optionally comprises a step of injecting to the skin lesion of the individual an anesthetic agent. The anesthetic agent can be administered in a separate injection or can be combined with the aqueous pharmaceutical composition and injected together.

In another embodiment, the method comprises the steps of identifying an individual suffering from inflammation and/or pain, and injecting to an affected joint of the individual any of the aqueous pharmaceutical compositions disclosed herein. The method optionally comprises a step of injecting to the affected joint of the individual an anesthetic agent. The anesthetic agent can be administered in a separate injection or can be combined with the pharmaceutical composition and injected together.

In some embodiments, the dose of the steroid injected is based on the potency of the steroid. In some embodiments, the amount of corticosteroid administered to an individual in a single dose is between 2 mg and 20 mg; 5 mg and 15 mg; and 5 mg and 10 mg. In some embodiments, the amount of corticosteroid administered to an individual in a single dose is about 2 mg, 5 mg, 8 mg, 10 mg, 15 mg and 20 mg.

In certain embodiments, the dosage of dexamethasone is about 3 to 20 mg/dose; the dosage of methylprednisolone is about 20 to 120 mg/dose, the dosage of prednisolone is about 20 to 120 mg/dose; the dosage of triamcinolone acetonide is about 20 to 120 mg/dose.

In some embodiments, the individual is injected with the pharmaceutical composition once every 1 to 12 weeks; 1 to 8 weeks; 1 to 4 weeks; 2 to 12 weeks; 4 to 12 weeks; 8 to 12 weeks; 2 to 8 weeks; or 2 to 4 weeks. In some embodiments, the individual is injected with the pharmaceutical composition about every 1, 2, 4, 6, 8, 10, or 12 weeks.

The methods and compositions disclosed herein are useful in treating an individual that is a mammal, such as a human, dog, or cat. The methods and compositions disclosed herein are particularly useful in treating humans.

Other Uses. Intralesional injection is a direct delivery of medication percutaneously into skin lesions. Intralesional injections are introduced into or performed within a lesion. The skin serves as a reservoir, allowing medication deposited in the dermis to be delivered over a period of time, resulting in prolonged therapy while avoiding or minimizing the adverse effects of systemic therapy.

Intra-articular injection is a procedure used in the treatment of inflammatory joint conditions, such as rheumatoid arthritis, psoriatic arthritis, gout, tendinitis, bursitis and occasionally osteoarthritis. A hypodermic needle is injected into the affected joint where it delivers an anti-inflammatory agent such as a corticosteroid.

The application discloses pharmaceutical compositions with a range of viscosities. The choice of the viscosity is in part dependent on the desired location of the injected pharmaceutical composition in the individual. For instance, when a localized amount of the pharmaceutical composition is desired, a pharmaceutical composition with a higher viscosity may be selected. Alternatively, if broader coverage of the pharmaceutical composition is desired, a pharmaceutical composition with a lower viscosity may be selected. In some embodiments, the method comprises administering the pharmaceutical composition via a transforaminal injection, wherein the pharmaceutical composition comprises between 0.5% and 1.5%, 1.0% and 1.5%, or 0.75% and 1.25%, of a viscosity enhancing agent. In some embodiments, the method comprises administering the pharmaceutical composition via an interlaminar injection, wherein the pharmaceutical composition comprises between 0.1% and 1.5%, 0.1% and 1.0%, 0.1% and 0.75%, 0.1% and 0.5%, 0.1% and 0.25%, 0.75% and 1.5%, 1.0% and 1.5%, or 0.75% and 1.25% of a viscosity enhancing agent. In some embodiments, the method comprises administering the pharmaceutical composition via a caudal injection, wherein the pharmaceutical composition comprises between 0.1% and 1.5%, 0.1% and 1.0%, 0.1% and 0.75%, 0.1% and 0.5%, 0.1% and 0.25%, 0.75% and 1.5%, 1.0% and 1.5%, or 0.75% and 1.25% of a viscosity enhancing agent. In some of the foregoing embodiments, the viscosity enhancing agent is hyaluronic acid or a salt thereof.

Syringeability and injectability. Syringeability is the ability of an injectable therapeutic to pass easily through a hypodermic needle on transfer from a vial prior to an injection. Syringeability includes such factors as ease of withdrawal, clogging and foaming tendencies, and accuracy of dose measurements. Injectability refers to the performance of the formulation during injection. Injectability includes pressure or force required for injection, evenness of flow, and freedom from clogging (i.e., no blockage of the syringe needle). The syringability and injectability is influenced in part by the viscosity of the pharmaceutical composition, the injection or transfer flow rate, and the needle characteristics (such as length and gauge).

Desirable characteristics of injectability include, for example, a smooth and continuous injection without undue force. Such an injection allows the person administrating the injection to maintain continuous control over the procedure without incurring undue strain.

The application discloses compositions that are easily syringeable and/or injectable into an individual. The application also discloses methods for injecting an individual with a pharmaceutical composition, wherein the injecting is easy and provides a continuous flow of the pharmaceutical composition. In some embodiments, the method comprises applying an injecting force of between 5 N and 90 N, 5 N and 50 N, 50N and 100 N, 5 N and 25 N, 25 N and 50 N, or 10 N and 40 N to the syringe. In some embodiments, the method comprises applying a force of no more than 5 N, no more than 7 N, no more than 10 N, no more than 15 N, no more than 17 N, no more than 21 N, no more than 27 N, no more than 29 N, no more than 33 N, no more than 38 N, no more than 39 N, no more than 46 N, no more than 59 N, no more than 70, no more than 78 N or no more than 90 N to the syringe. In some embodiments, the method comprises applying a force of about 5 N, about 7 N, about 10 N, about 15 N, about 17, about 21 N, about 27 N, about 29 N, about 33 N, about 38 N, about 39 N, about 46 N, about 59 N, about 70, about 78 N or about 90 N to the syringe. In some embodiments, the injection force results in the injection of the pharmaceutical composition at a rate (i.e. extrusion rate) of about 0.4"/min, about 0.5"/min, about 0.6"/min, about 0.7"/min, about 0.8"/min, about 0.9"/min, about 1.0"/min, about 1.1"/min, about 1.2"/min, about 1.3"/min, about 1.4"/min, about 1.5"/min, about 1.75"/min, about 2.0"/min, about 2.25"/min, or at about 2.36"/min.

In any of the foregoing embodiments, the syringe comprises a needle having needle gauge of 19, 20, 21, 22, 23, 24, or 25. In one embodiment, the syringe comprises a needle having needle gauge of 25.

The application discloses a method for injection which reduces the "stringing effect". The stringing effect refers to a phenomenon that when the injection of the pharmaceutical composition into an individual is finished, the remaining composition in the bore of the needle used in the injection comes into contact with the individual. For instance, when the needle is withdrawn from the target site, the remaining composition in the bore of the needle is drawn out due to the viscous nature of the composition and elongates like string. The needle may leave a trail of the composition as it exits the individual, potentially exposing unintended areas and tissues to the composition. Unintended placement of the composition can lead to undesirable effects such as arachnoditis caused from an epidural injection. In some instances, upon withdrawal of the needle the composition injected into the target site may elongate and stretch and may come into contact with unintended areas and tissues of the individual.

In some embodiments, the methods and compositions disclosed herein reduce the occurrence of the stringing effect. In some embodiments, upon withdrawal from the injection site, no pharmaceutical composition disclosed herein exits the needle into the individual. In some embodiments, the pharmaceutical composition enters an individual only when an injection force is applied. In some embodiments, the composition makes a clean break with very little stringing upon separation or division.

In some embodiments, the application discloses a method for treating inflammation and/or pain in an individual in need thereof, comprising injecting an aqueous pharmaceutical composition disclosed herein into the epidural, intralesional, or intra-articular space of the individual; and wherein the method comprises one or more of the steps selected from the group consisting of 1) applying a force of less than 5 N, less than 7 N, less than 10 N, less than 15 N, less than 17, or less than 21 N to inject the aqueous pharmaceutical composition at a rate of about 0.4"/min, about 0.5"/min, about 0.6"/min, about 0.7"/min, about 0.8"/ min, about 0.9"/min, about 1.0"/min, about 1.1"/min, about 1.2"/min, about 1.3"/min, about 1.4"/min, about 1.5"/min, about 1.75"/min, about 2.0"/min, about 2.25"/min, or at about 2.36"/min.; and 2) injecting the aqueous pharmaceutical composition once every 1 to 12 weeks.

In some embodiments, the application discloses a method for treating inflammation and/or pain in an individual in need thereof, comprising injecting an aqueous pharmaceutical composition disclosed herein into the epidural, intralesional, or intra-articular space of the individual; and wherein the method comprises one or more of the steps selected from the group consisting of 1) applying a force of less than 21 N to inject the aqueous pharmaceutical composition at a rate of about 0.5"/min; and 2) injecting the aqueous pharmaceutical composition once every 1 to 12 weeks.

In some embodiments, the application discloses a method for treating inflammation and/or pain in an individual in need thereof, comprising injecting any of the exemplary formulations in Table 1 into the epidural, intralesional, or intra-articular space of the individual; and wherein the method comprises one or more of the steps selected from the group consisting of 1) applying a force of less than 5 N, less than 7 N, less than 10 N, less than 15 N, less than 17, or less than 21 N to inject the aqueous pharmaceutical composition at a rate of about 0.4"/min, about 0.5"/min, about 0.6"/min, about 0.7"/min, about 0.8"/min, about 0.9"/min, about 1.0"/ min, about 1.1"/min, about 1.2"/min, about 1.3"/min, about 1.4"/min, about 1.5"/min, about 1.75"/min, about 2.0"/min, about 2.25"/min, or at about 2.36"/min.; and 2) injecting the aqueous pharmaceutical composition once every 1 to 12 weeks. In further embodiments, the step of injecting the aqueous pharmaceutical composition occurs about every 1, 2, 4, 6, 8, 10, or 12 weeks.

In some embodiments, the application discloses a method for treating inflammation and/or pain in an individual in need thereof, comprising injecting any of the exemplary formulations in Table 1 into the epidural space of the individual; and wherein the method comprises one or more of the steps selected from the group consisting of 1) applying a force of less than 21 N to inject the aqueous pharmaceutical composition at a rate of about 0.5"/min; and 2) injecting the aqueous pharmaceutical composition once every 1 to 12 weeks. In further embodiments, the step of injecting the aqueous pharmaceutical composition occurs about every 1, 2, 4, 6, 8, 10, or 12 weeks.

In some embodiments, the application discloses the use of an aqueous pharmaceutical composition, as described herein, in the manufacture of a formulation for the treatment of inflammation and/or pain in an individual in need thereof, wherein the formulation is injected into the individual.

The term "and/or" includes subject matter in the alternative as well as subject matter in combination. For instance, "x and/or y" includes "x or y" and "x and y".

The term "about" includes and describes the value or parameter per se. For example, "about x" includes and describes "x" per se. In certain embodiment, the term "about" when used in association with a measurement, or used to modify a value, a unit, a constant, or a range of values, refers to variations of +1-10%. In some embodiments, the term "about" when used in association with a measurement, or used to modify a value, a unit, a constant, or a range of values, refers to variations of +5%. In some embodiments, the term "about" when used in association with a measurement, or used to modify a value, a unit, a constant, or a range of values, refers to variations of +10%.

The term "between" includes and describes the value or parameter per se. For example, "between x and y" includes and describes "x" and "y" per se.

Any one of the foregoing embodiments may be combined with one or more other embodiments disclosed herein. For instance, by combining various embodiments disclosed herein a pharmaceutical composition comprising soluble dexamethasone sodium phosphate, soluble methylprednisolone, and sodium hyaluronate in an aqueous solution such as water, wherein the pharmaceutical composition has a viscosity of between 1 kcP and 200 kcP, is provided by this application. In another instance, by combining various embodiments disclosed herein a method of treating inflammation and/or pain in an individual in need thereof comprising injecting a pharmaceutical composition comprising soluble dexamethasone sodium phosphate, soluble methylprednisolone, and sodium hyaluronate in an aqueous solution such as water, wherein the pharmaceutical composition has a viscosity of between 1 kcP and 200 kcP, is provided by this application.

The following examples further illustrate embodiments of the present application. These examples are intended merely to be illustrative of embodiments of the present application and are not to be construed as being limiting.

EXAMPLES

Example 1. Preparation of Dexamethasone Sodium Phosphate (SP-102) Formulation Test Samples This example describes the formulations of dexamethasone sodium phosphate (SP-102) used in the physical and chemical analysis, dissolution, in vivo, and histopathological studies detailed in Examples 2-5.

Dexamethasone sodium phosphate, $Na_2HPO_4 \cdot 7H_2O$, $NaH_2PO_4 \cdot H_2O$, and NaCl were combined in HPLC grade water. Sodium hyaluronate (HA, 1.56 MDa) was slowly added and the resulting mixture was stirred overnight to yield a clear colorless gel. A batch formulation of 100 mL was typically prepared. The amount of dexamethasone sodium phosphate used was equivalent to 5.0 mg/mL dexamethasone. The amount of added sodium hyaluronate was varied as shown in Table 2.

TABLE 2

Compositions of SP-102 formulations with varying amounts of sodium hyaluronate.

| Reagent | concentration (mg/mL) | SP-102 (0.5% HA) | SP-102 (0.75% HA) | SP-102 (1.0% HA) | SP-102 (1.25% HA) |
|---|---|---|---|---|---|
| | | mg (per 100 mL batch) | | | |
| dexamethasone sodium phosphate | 6.58 | 658 | 658 | 658 | 658 |
| sodium hyaluronate | as needed | 500 | 750 | 1000 | 1250 |
| $Na_2HPO_4 \cdot 7H_2O$ | 2.75 | 275 | 275 | 275 | 275 |
| $NaH_2PO_4 \cdot H_2O$ | 0.65 | 65 | 65 | 65 | 65 |
| NaCl | 7.0 | 700 | 700 | 700 | 700 |
| water | q.s. | 97082 | 97552 | 97302 | 97052 |
| Total weight (g)= | | 100.0 | 100.0 | 100.0 | 100.0 |

The inventors previously described a pharmaceutical composition comprising both an insoluble form and a soluble form of a corticosteroid in combination a viscosity enhancing agent such as hyaluronic acid (PCT International Publication No. WO 2014/116876). As discussed above, new safety recommendations restrict the use of particulate steroids in transforaminal injections. Table 3 provides a comparison of formulation SP-102 of the present invention with the particulate formulation SP-101.

TABLE 3

Comparison of Formulations SP-101 and SP-102.

| Reagent | Concentration (mg/mL) | |
|---|---|---|
| | SP-101 | SP-102 |
| dexamethasone acetate | 4.43 | — |
| (equivalent to dexamethasone) | 4.0 | — |

TABLE 3-continued

Comparison of Formulations SP-101 and SP-102.

| Reagent | Concentration (mg/mL) | |
|---|---|---|
| | SP-101 | SP-102 |
| dexamethasone sodium phosphate | 1.32 | 6.58 |
| (equivalent to dexamethasone) | 1.0 | 5.0 |
| sodium hyaluronate | 12.5 | 12.5 |
| $Na_2HPO_4 \cdot 7H_2O$ | 2.75 | 2.75 |
| $NaH_2PO_4 \cdot H_2O$ | 0.65 | 0.65 |
| NaCl | 6.5 | 7.0 |
| water for injection | q.s. | q.s. |

Example 2. Physical and Chemical Analysis of SP-102 Formulations

This Example describes the physical and chemical analysis for SP-102 formulations containing 0.5%, 0.75%, 1.0%, and 1.25% sodium hyaluronate. The appearance of the samples and the measured pH is presented in Table 4. Analysis of dexamethasone sodium phosphate in the samples by HPLC is also presented in Table 4.

TABLE 4

Physical and Chemical Analysis of SP-102 Formulations.

| Sample | Appearance | pH | HPLC Assay |
|---|---|---|---|
| SP-102 (0.5% HA) | colorless clear gel | 7.2 | not measured |
| SP-102 (0.75% HA) | colorless clear gel | 7.2 | 103.6% |
| SP-102 (1.0% HA) | colorless clear gel | 7.2 | 107.7% |
| SP-102 (1.25% HA) | colorless clear gel | 7.2 | 109.5% |

The viscosity of the SP-102 formulations was determined using a Brookfield Viscometer with cone-and-plate CP-52 spindle and a rotor speed of 20 rpm (5 min, 25° C.). The viscosity results are summarized in Table 5.

TABLE 5

Viscosity of SP-102 Formulations.

| Sample | Viscosity (cps) |
|---|---|
| SP-102 (0.5% HA) | 334 |
| SP-102 (0.75% HA) | 1108 |
| SP-102 (1.0% HA) | 2110 |
| SP-102 (1.25% HA) | 3647 |

Example 3. Dissolution Study of SP-102 Formulations

This Example describes the dissolution of SP-102 formulations containing 0.5%, 0.75%, 1.0%, and 1.25% sodium hyaluronate.

The dissolution study was performed using a Type 2 USP Dissolution Apparatus with paddle. The medium (0.05 M phosphate buffer, pH 7.0, 0.5% TWEEN®-80) was stirred at 25±2 rpm (37±0.5° C.). Samples (2 mL) were withdrawn at various time points and analyzed for dexamethasone sodium phosphate content by HPLC analysis. The HPLC conditions used were as follows:

Column: Waters XTerra RP18 column, 3.5 μm, 4.6×150 mm

Mobile Phase (isocratic): 0.1% Phosphoric Acid in water: Acetonitrile (70:30)

Column Temperature: 40° C.

Autosampler Temperature: Ambient

Detection: UV 242 nm

Flow Rate: 1 mL/min

Injection Volume: 10 μL

Run time: 10 min

Diluent: Dissolution Medium

The results of the dissolution study are presented in Tables 6 and 7.

TABLE 6

Dissolution Profiles of SP-102 Formulations.

| | | % dexamethasone sodium phosphate released | | | | | | |
|---|---|---|---|---|---|---|---|---|
| Sample | Sample No. | 5 min | 10 min | 20 min | 40 min | 60 min | 120 min | Infinity* |
| SP-102 (0.5% HA) | 1 | 31.1 | 60.9 | 95.5 | 100.2 | 101.2 | 101.9 | 101.5 |
| | 2 | 18.3 | 50.0 | 93.4 | 100.2 | 100.3 | 101.0 | 100.5 |
| SP-102 (0.75% HA) | 1 | 10.6 | 18.1 | 30.9 | 55.4 | 78.1 | 105.5 | 109.4 |
| | 2 | 13 | 21.4 | 35.2 | 63.8 | 84.4 | 111.1 | 113.4 |
| SP-102 (1.0% HA) | 1 | 9.5 | 15.5 | 25.9 | 43.3 | 59.5 | 97.0 | 124.0 |
| | 2 | 7.7 | 13.3 | 23.3 | 40.5 | 54.8 | 93.6 | 112.6 |
| SP-102 (1.25% HA) | 1 | 6.9 | 10.9 | 18.9 | 31.3 | 42.5 | 70.0 | 116.2 |
| | 2 | 7.2 | 11.6 | 19.7 | 32.9 | 43.7 | 70.4 | 116.6 |

*Infinity at 250 rpm for 15 min.

TABLE 7

Dissolution Profiles of SP-102 Formulations (Normalized to Infinity with Completed Dissolution).

| | Sample | | | |
|---|---|---|---|---|
| Time (min) | SP-102 (0.5% HA) | SP-102 (0.75% HA) | SP-102 (1.0% HA) | SP-102 (1.25% HA) |
| 5 | 24.5 | 10.6 | 7.3 | 6.1 |
| 10 | 55.0 | 17.8 | 12.2 | 9.7 |
| 20 | 93.6 | 29.7 | 20.8 | 16.6 |
| 40 | 99.2 | 53.5 | 35.4 | 27.6 |
| 60 | 99.8 | 73.0 | 48.4 | 37.0 |
| 120 | 100.5 | 97.2 | 80.6 | 60.3 |

The data presented in Tables 6 and 7 demonstrate that sample SP-102 (0.5% HA) released more than 90% of dexamethasone sodium phosphate within 20 minutes. The release rate decreased with increasing amounts of sodium hyaluronate in the SP-102 formulations. Each sample released all of the dexamethasone sodium phosphate after mixing in release media at 250 rpm for 15 minutes. However, only approximately 60% and 80% of the dexamethasone sodium phosphate was released in samples SP-102 (1.25% HA) and SP-102 (1.0% HA), respectively, after 2 hours at 25 rpm (Table 7). The data also reveals that there is a non-linear dependency of sodium hyaluronate content on the studied release profiles (FIG. 1).

Figure 2:
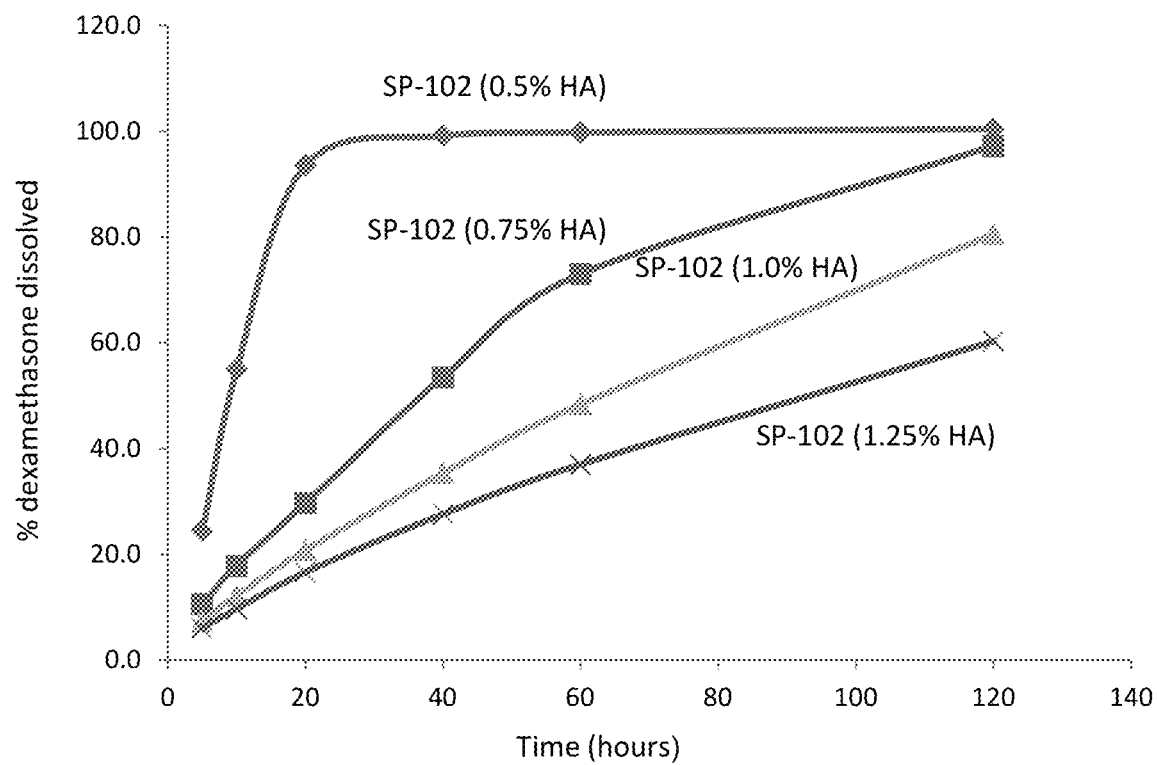
FIG. 2 shows the dissolution profile of SP-102 formulations in phosphate buffer, (0.05 M, pH 7).

Similar release profiles were obtained for these samples when the dissolution study was performed in medium lacking 0.5% TWEEN®-80, indicating that the surfactant (TWEEN®-80) has no significant impact on the release profile of the SP-102 formulations (FIG. 2).

Example 4. Stability Study of SP-102 Formulations

This Example describes the stability of SP-102 (1.25% HA) formulations.

The stability study was performed under accelerated conditions. Following aging, samples were analyzed by HPLC and evaluated for impurities (known impurity: dexamethasone; unknown impurities: RRT 0.97, RRT 0.89, RRT 1.47). The stability results are presented as a percentage of the control (refrigerated sample). The HPLC conditions used were as follows:

Column: Waters XTerra RPC18 column, 5 μm, 4.6×250 mm

Mobile Phase A (MP A): 0.02 M ammonium formate

Mobile Phase B (MP B): acetonitrile

Column Temperature: 40° C.

Detection: UV 242 nm

Gradient Conditions:

| Time (min) | MP A (%) | MP B (%) |
|---|---|---|
| 0 | 90 | 10 |
| 2 | 90 | 10 |
| 20 | 40 | 60 |
| 24 | 40 | 60 |
| 24.1 | 90 | 10 |
| 30 | 90 | 10 |

Injection Volume: 50 µL
Run time: 30 min
Diluent: 30% acetonitrile in 0.02 M ammonium formate
The results of the stability study are presented in Table 8.

TABLE 8

Stability Summary of SP-102 (1.25% HA).

| Storage Temperature (° C.) | Time (days) | Assay (% of Control) | % Impurity (Dexamethasone) | % Unknown Impurities |
|---|---|---|---|---|
| 2-8 | 72 | 100.0 | 0.08 | 0.00 (RRT 0.97) |
|  |  |  |  | 0.00 (RRT 0.89) |
|  |  |  |  | 0.18 (RRT 1.47) |
| room temperature | 72 | 99.6 | 0.11 | 0.25 (RRT 0.97) |
|  |  |  |  | 0.00 (RRT 0.89) |
|  |  |  |  | 1.71 (RRT 1.47) |
| 50 | 7 | 100.4 | 0.33 | 0.25 (RRT 0.97) |
|  |  |  |  | 0.00 (RRT 0.89) |
|  |  |  |  | 1.23 (RRT 1.47) |
| 50 | 14 | 99.6 | 0.55 | 0.25 (RRT 0.97) |
|  |  |  |  | 0.11 (RRT 0.89) |
|  |  |  |  | 1.51 (RRT 1.47) |
| 50 | 34 | 98.4 | 1.08 | 0.25 (RRT 0.97) |
|  |  |  |  | 0.17 (RRT 0.89) |
|  |  |  |  | 1.74 (RRT 1.47) |

The stability data demonstrates that SP-102 (1.25% HA) is stable at ambient room temperature up to 2.4 months or at 50° C. for at least 34 days with less than 2% degradation. The known impurity (dexamethasone) was increased to 1.1% and the unknown impurity (RRT 1.47) was increased to 1.7%. The stability of SP-102 (1.25% HA) is similar to that of commercial dexamethasone sodium phosphate containing sodium bisulfate (antioxidant) and benzyl alcohol (preservative).

Example 5. In Vivo Study of SP-102 Formulations

This example describes the in vivo studies of SP-102 formulations containing 0.5%, 1.0%, and 1.25% sodium hyaluronate.

The in vivo studies were performed using two pigs. The epidural space of both animals was accessed at the same anatomical locations: between the L4 and L5 vertebrae and between the last thoracic and L1 vertebrae. Several test formulations were injected into the epidural space. Some of the formulations were injected separately, whereas other formulations were compounded in the operating room. The formulations that were compounded in the operating room were combinations of commercial dexamethasone (4 mg/mL) and a contrast agent, either in liquid (ISOVUE® 300) or powder from. Following injection of the test formulations, several fluoroscopic cines were recorded at 15 min. intervals in order to monitor diffusion of the test formulations in the epidural space.

The animals were subsequently repositioned on supine recumbency and the vertebral arteries were canulated from the left subclavian artery following a seldinger technique access on the right femoral artery. The vertebral artery was used to deliver the test formulations while fluoroscopic cines were recorded from the brain with special interest on the brainstem. The right vertebral artery was used in one animal (animal #1) and the left vertebral artery was used in the second animal (animal #2).

Epidural Injection Time Course

Animal #1 was injected with three separate formulations. The formulations were as follows:

Injection 1 (control): 2 mL of dexamethasone sodium phosphate (4 mg/mL) and 647 iohexol (a contrast agent).

Injection 2: 2 mL SP-102 (0.5% HA) and 647 mg iohexol.

Injection 3: 2 mL SP-102 (1.25% HA) and 647 mg iohexol.

Figure 3A:
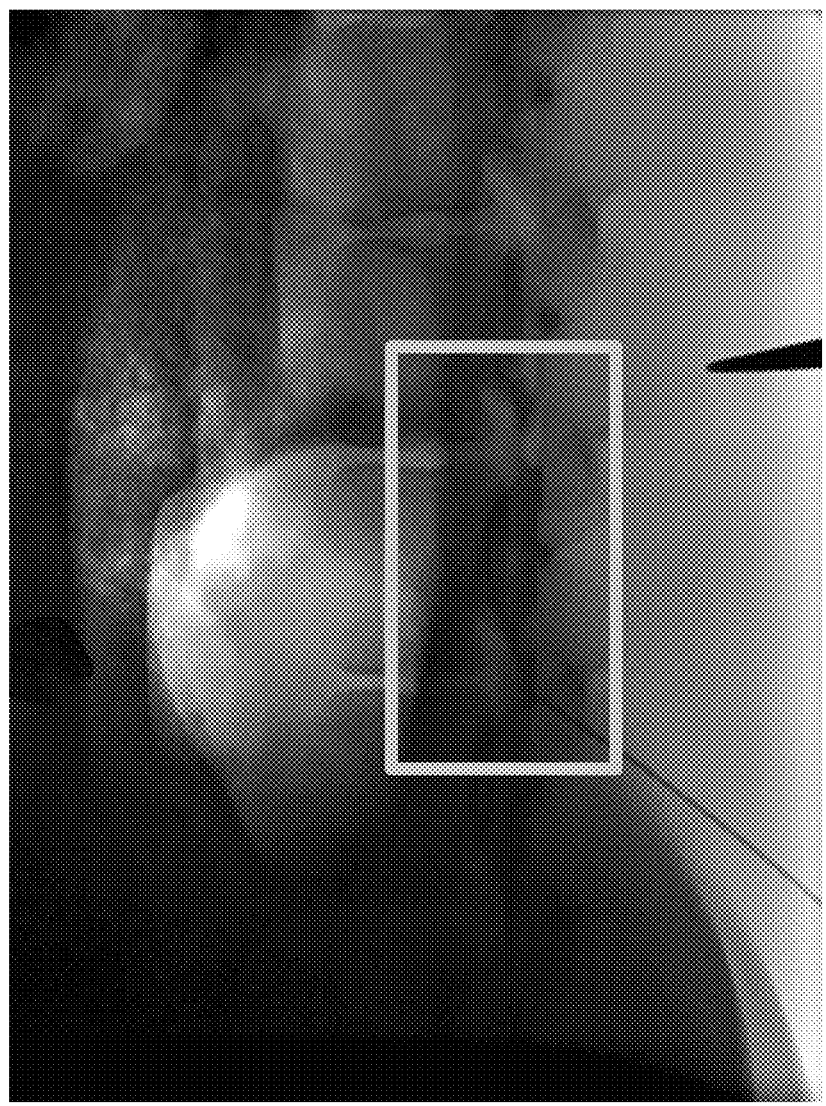
FIG. 3A, FIG. 3B, and FIG. 3C show an image of animal #1 recorded immediately post-injection with the control (FIG. 3A), or formulations SP-102 with 0.5% HA (FIG. 3B), or SP-102 with 1.25% HA (FIG. 3C).
Figure 3B:
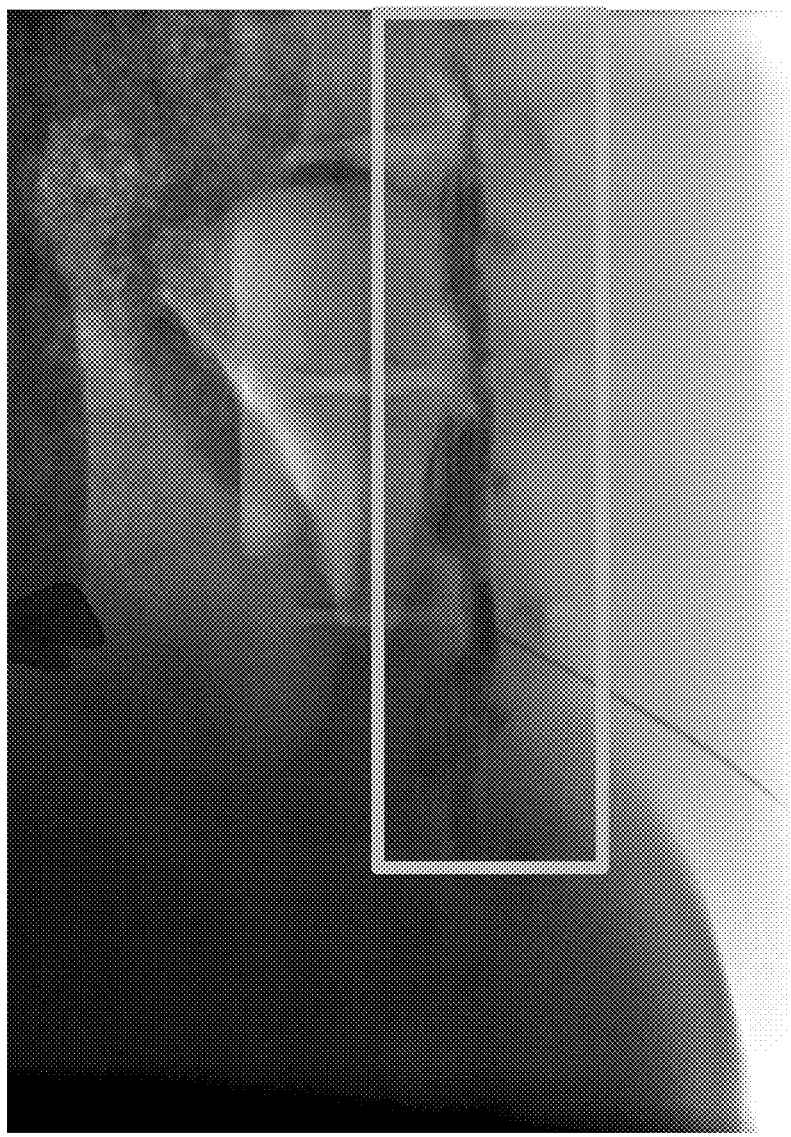
Figure 3C:
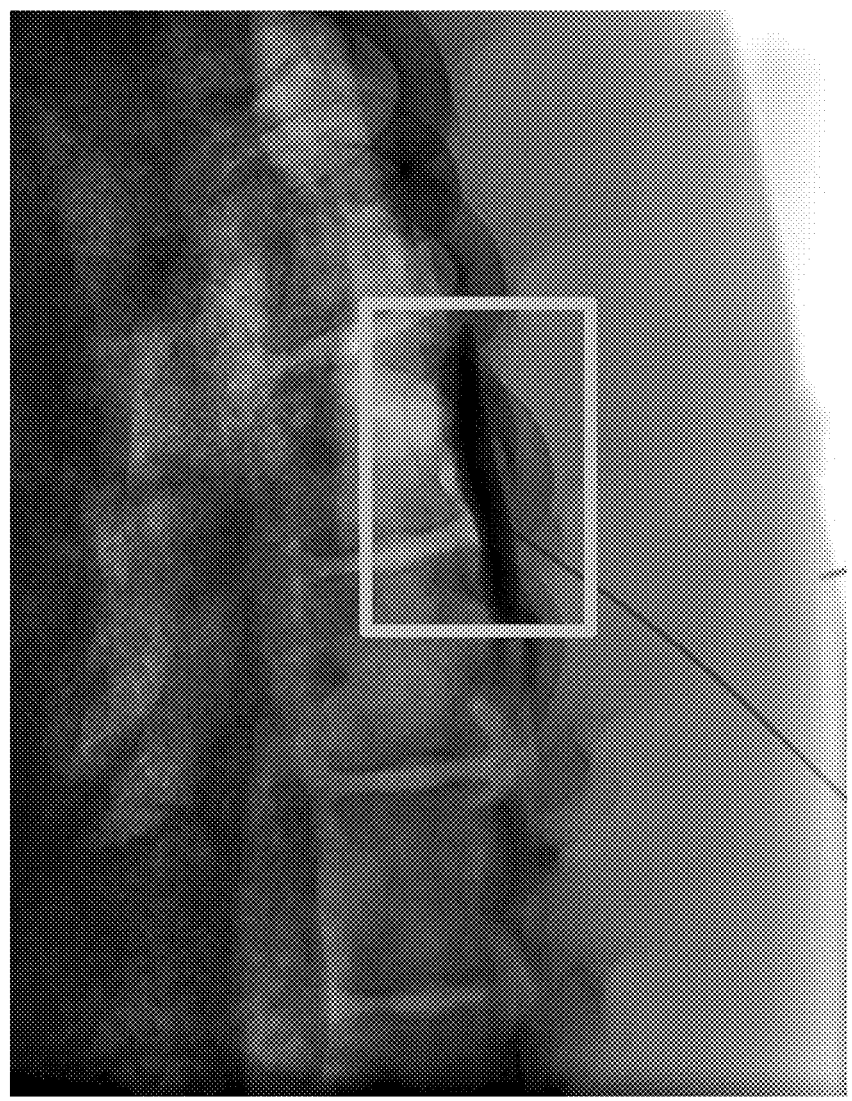
Figure 4A:
FIG. 4A, FIG. 4B, and FIG. 4C show an image of animal #1 recorded 30 minutes post-injection with the control (FIG. 4A), or formulations SP-102 with 0.5% HA (FIG. 4B), or SP-102 with 1.25% HA (FIG. 4C).
Figure 4B:
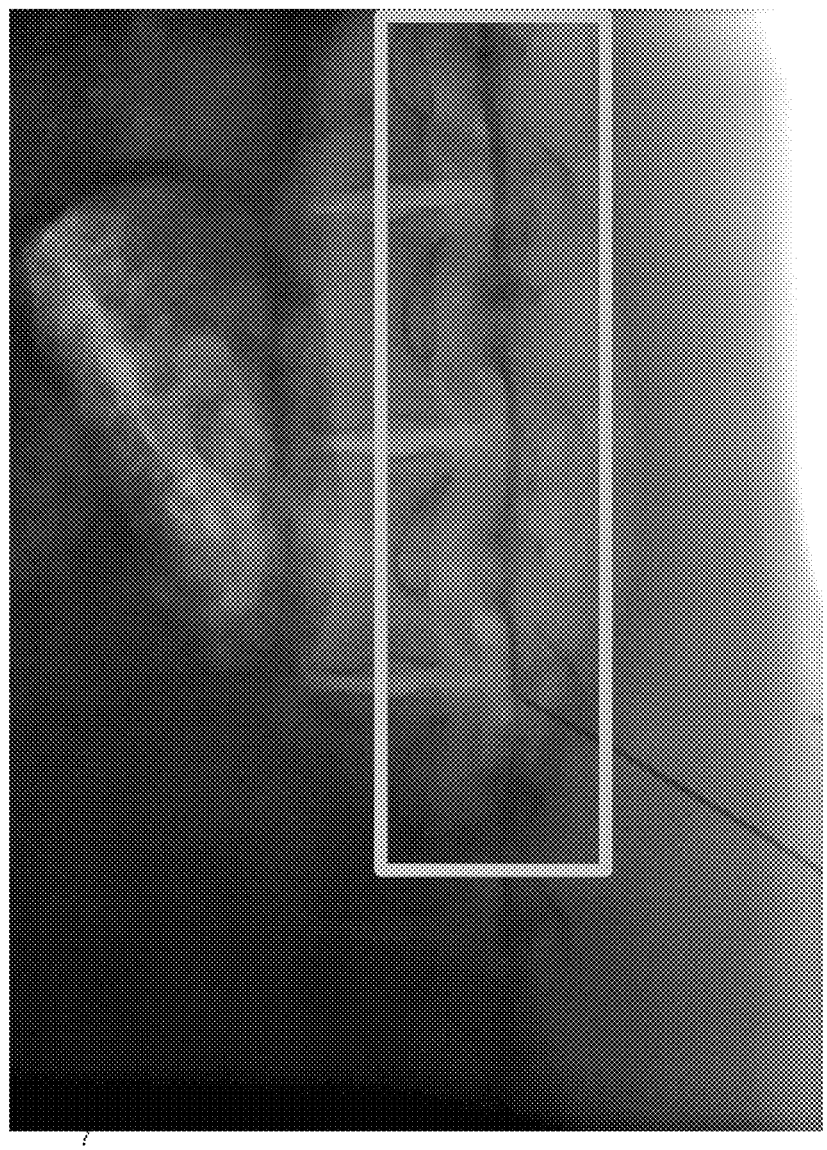
Figure 4C:
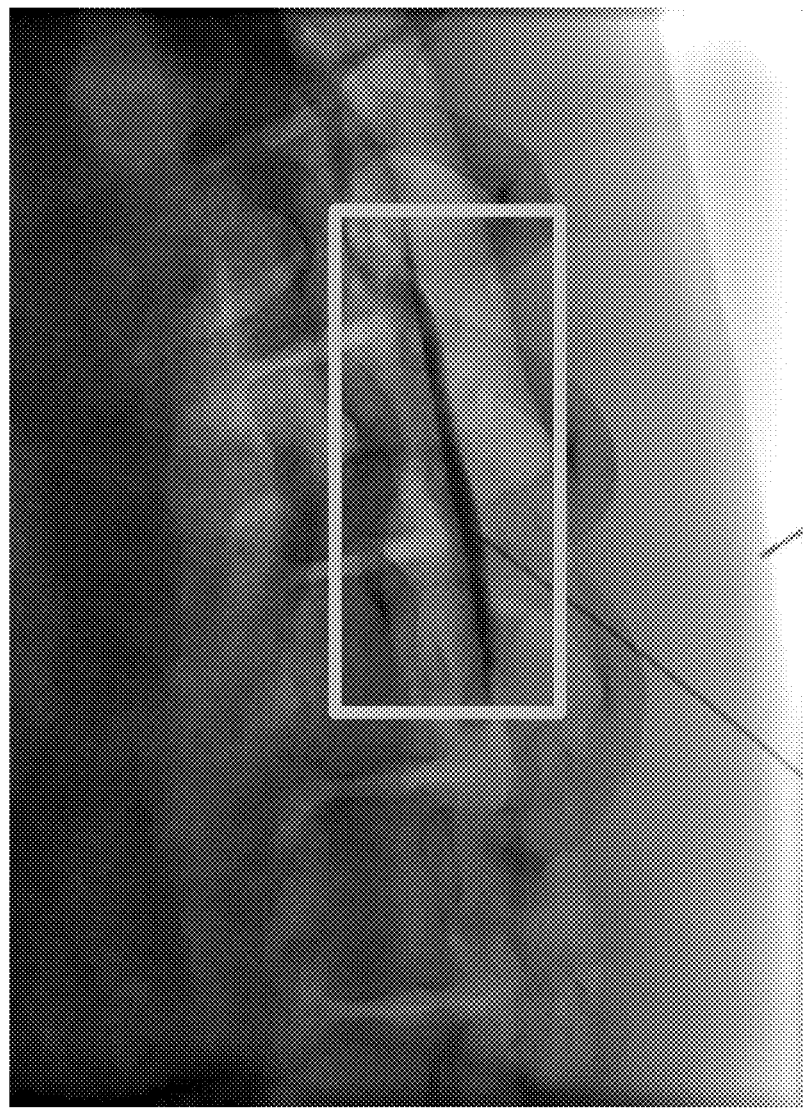
Figure 5A:
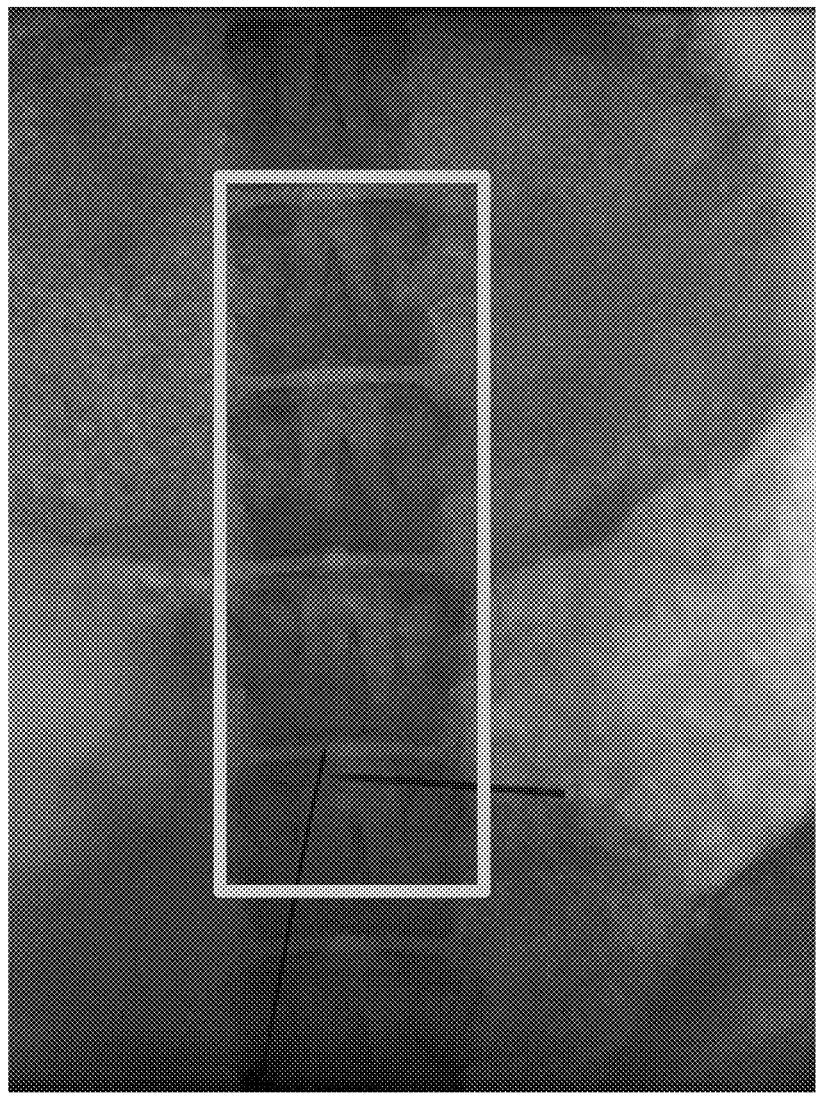
FIG. 5A, FIG. 5B, and FIG. 5C show an image of animal #1 recorded 60 minutes post-injection with the control (FIG. 5A), or formulations SP-102 with 0.5% HA (FIG. 5B), or SP-102 with 1.25% HA (FIG. 5C).
Figure 5B:
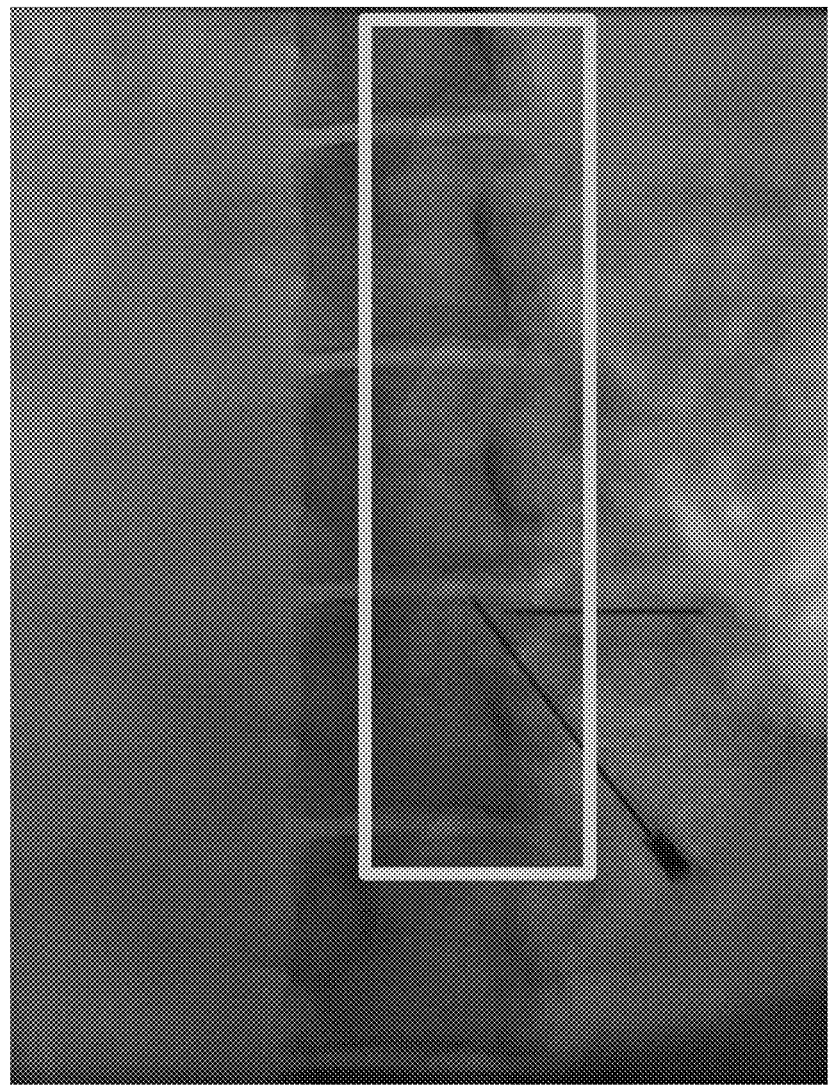
Figure 5C:
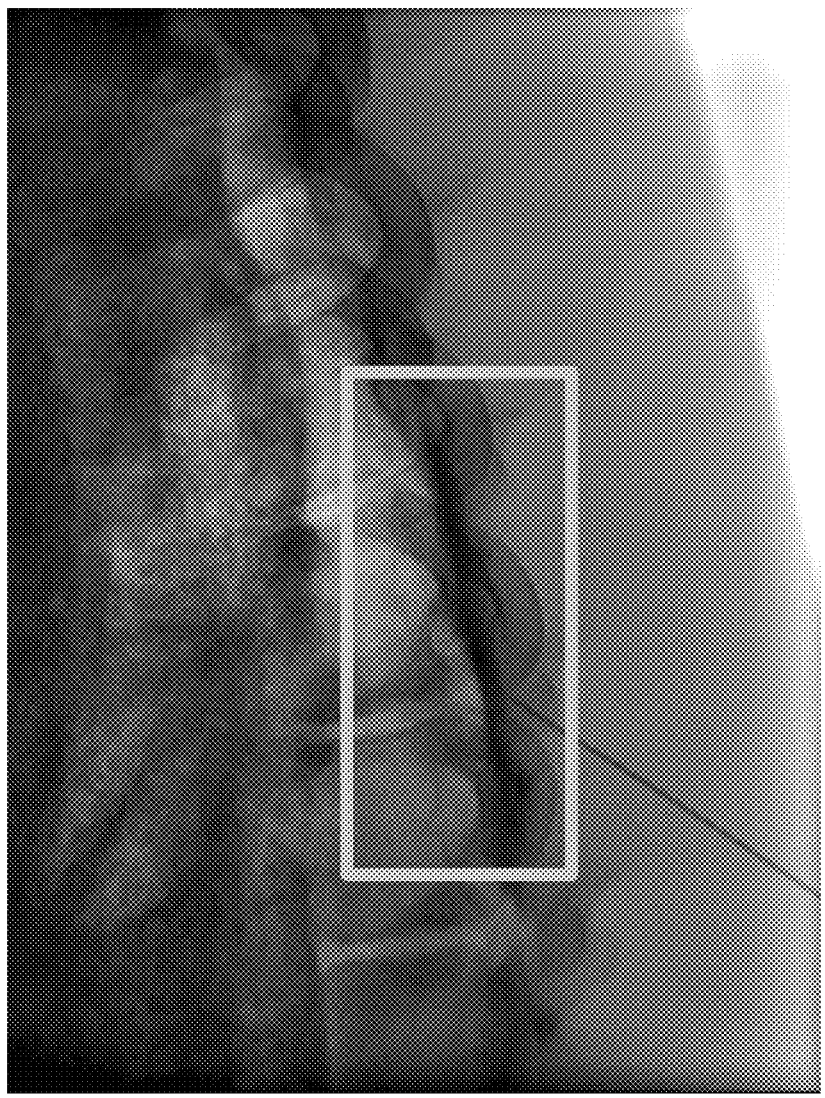
Figure 6A:
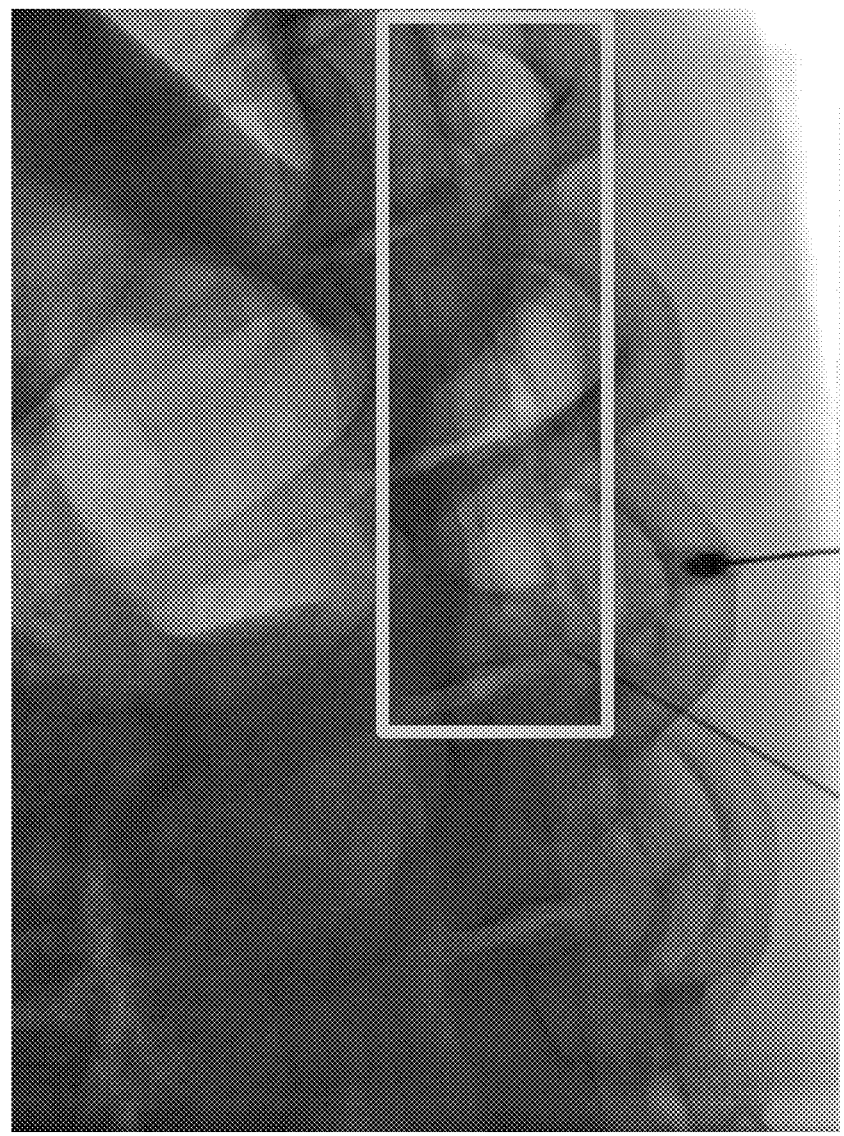
FIG. 6A and FIG. 6B show an image of animal #1 recorded 120 minutes post-injection with the control (FIG. 6A), or formulation SP-102 with 1.25% HA (FIG. 6B).
Figure 6B:
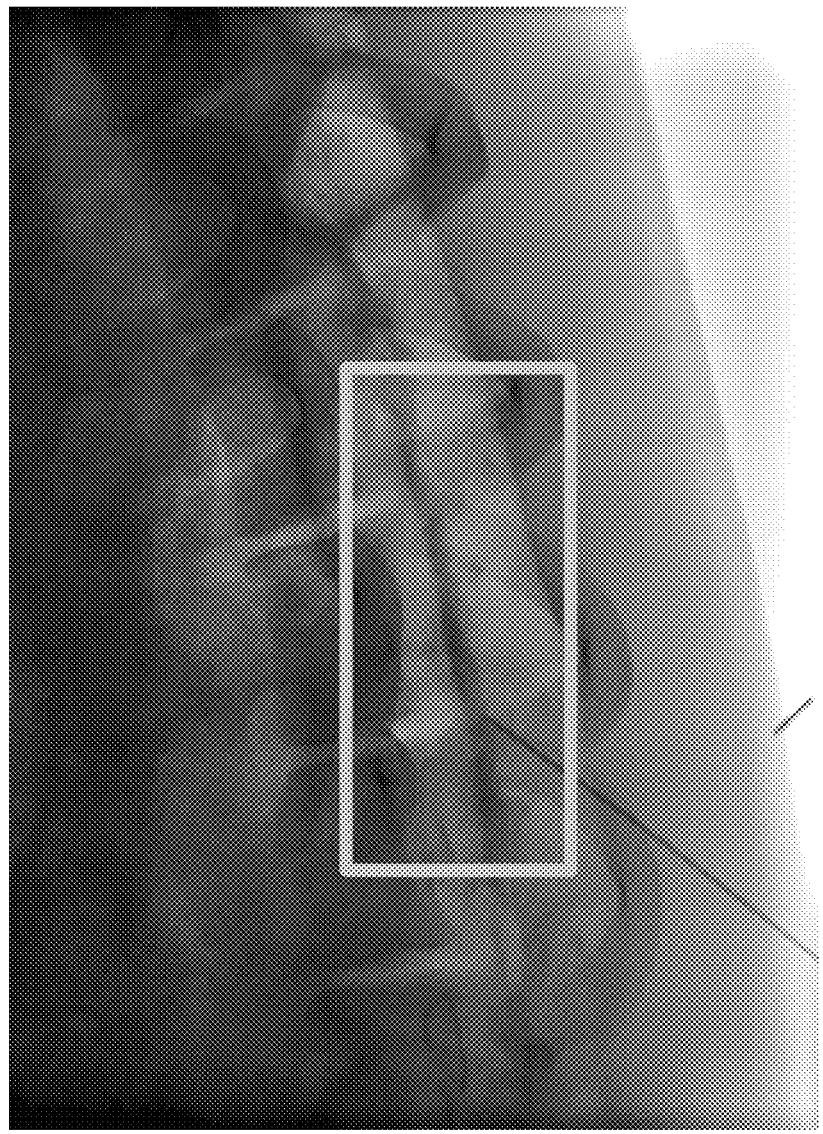
Figure 7:
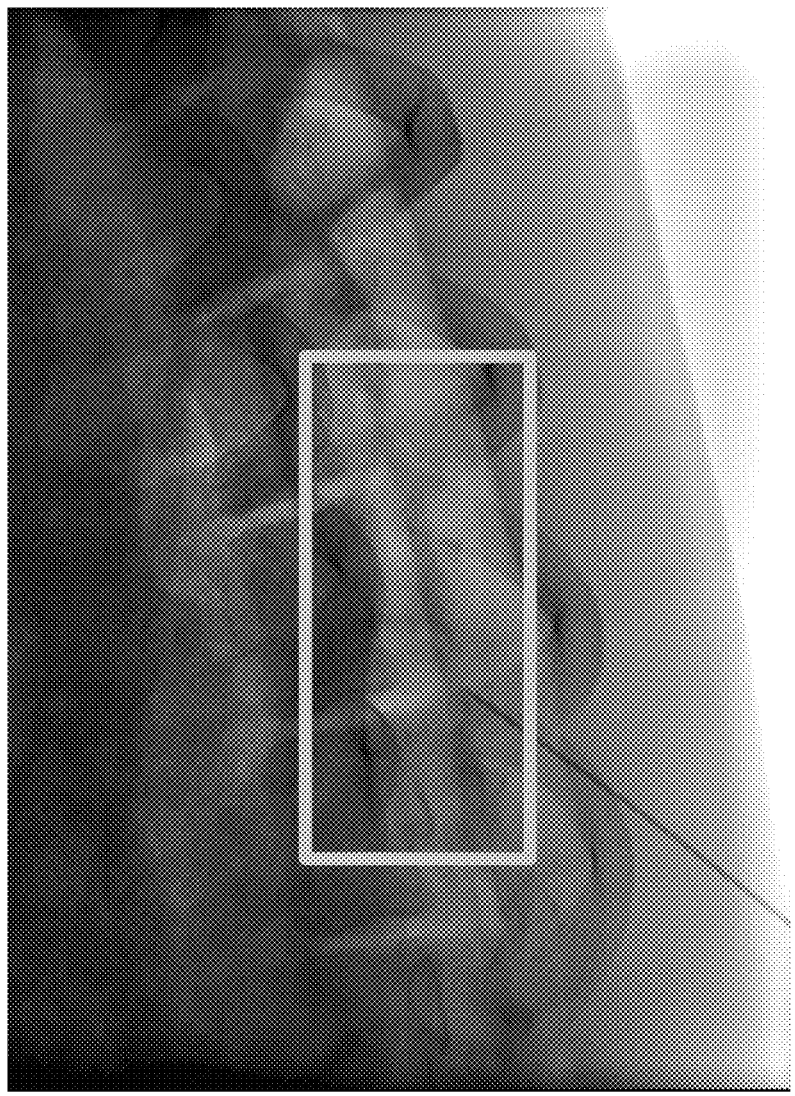
FIG. 7 shows the image recorded 180 minutes post-injection in animal #1 injected with formulation SP-102 (1.25% HA).

The post-injection images, recorded immediately following injection of animal #1, are shown in FIGS. 3A-3C for the control and for formulations SP-102 (0.5% HA) and SP-102 (1.25% HA). The corresponding images, recorded 30 min and 60 min after injection, are presented in FIGS. 4A-4C and FIGS. 5A-5C, respectively. The images recorded 120 min after injection for the control and formulation SP-102 (1.25% HA) are shown in FIGS. 6A-6B. Lastly, the image recorded 180 min post-injection for formulation SP-102 (1.25% HA) is shown in FIG. 7.

Animal #2 was injected with two separate formulations. The formulations were as follows:

Injection 1: 2 mL SP-102 (1.0% HA) and 647 mg iohexol.

Injection 2: 2 mL SP-102 (1.25% HA) and 647 mg iohexol.

Figure 8A:
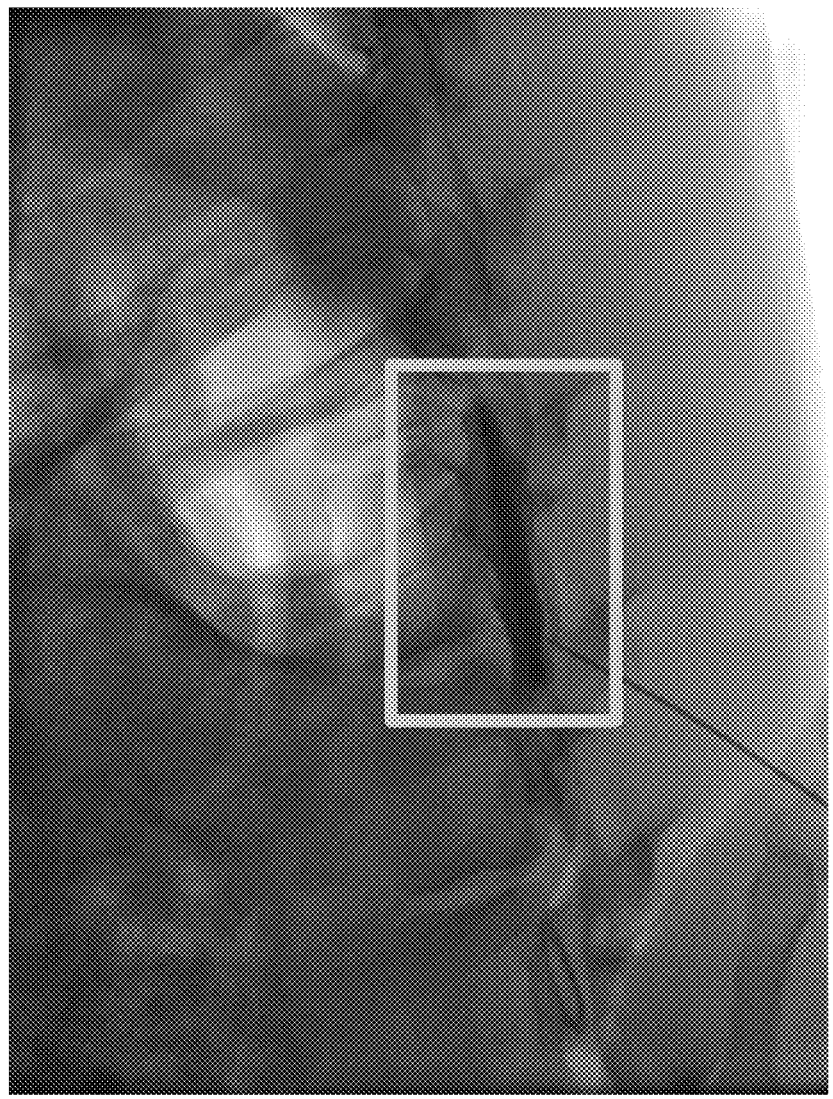
FIG. 8A and FIG. 8B show an image of animal #2 recorded immediately post-injection with formulations SP-102 with 1.0% HA (FIG. 8A) and SP-102 with 1.25% HA (FIG. 8B).
Figure 8B:
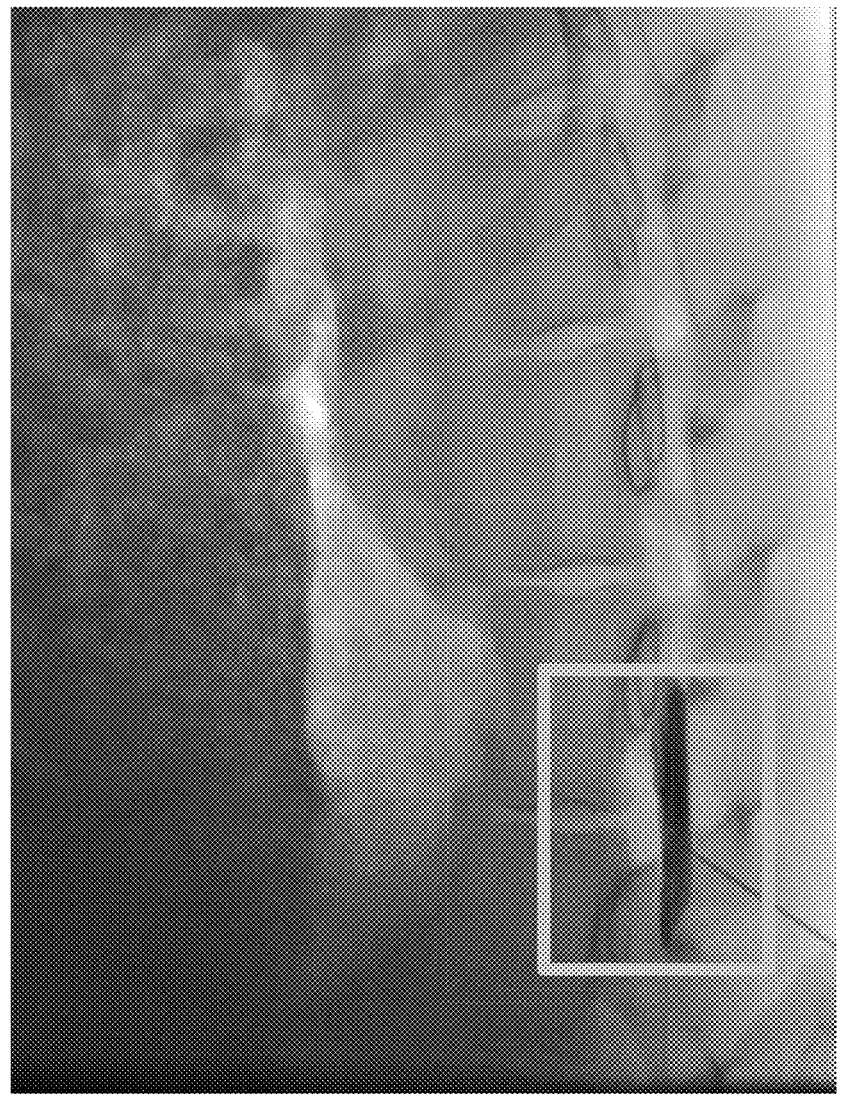
Figure 9A:
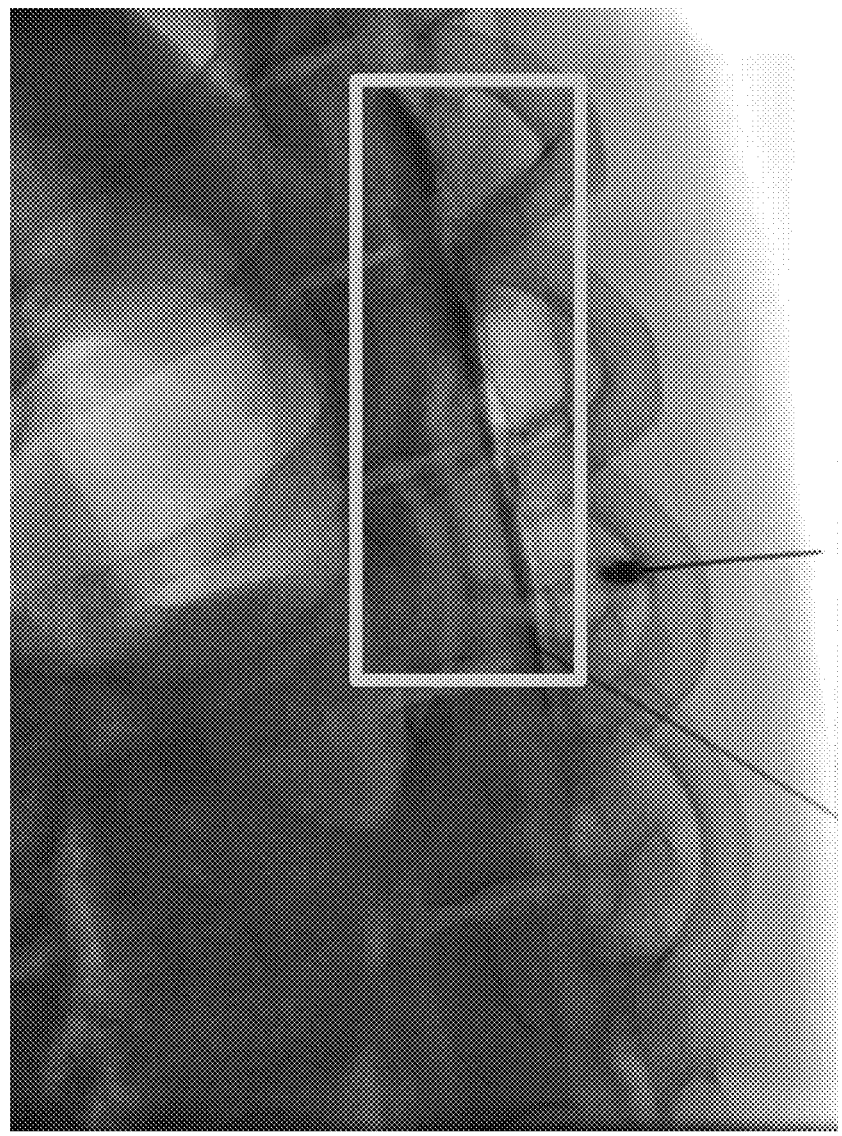
FIG. 9A and FIG. 9B show an image of animal #2 recorded 30 minutes post-injection with formulations SP-102 with 1.0% HA (FIG. 9A) and SP-102 with 1.25% HA (FIG. 9B).
Figure 9B:
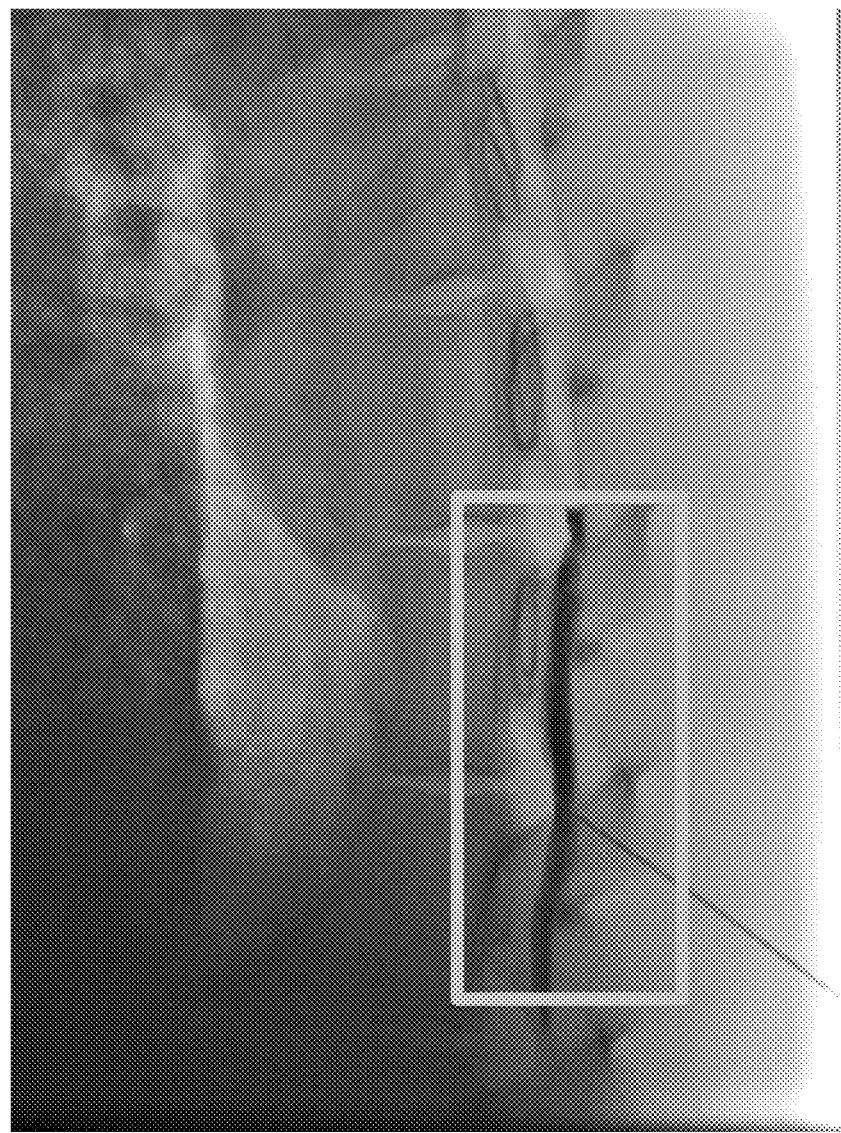
Figure 10A:
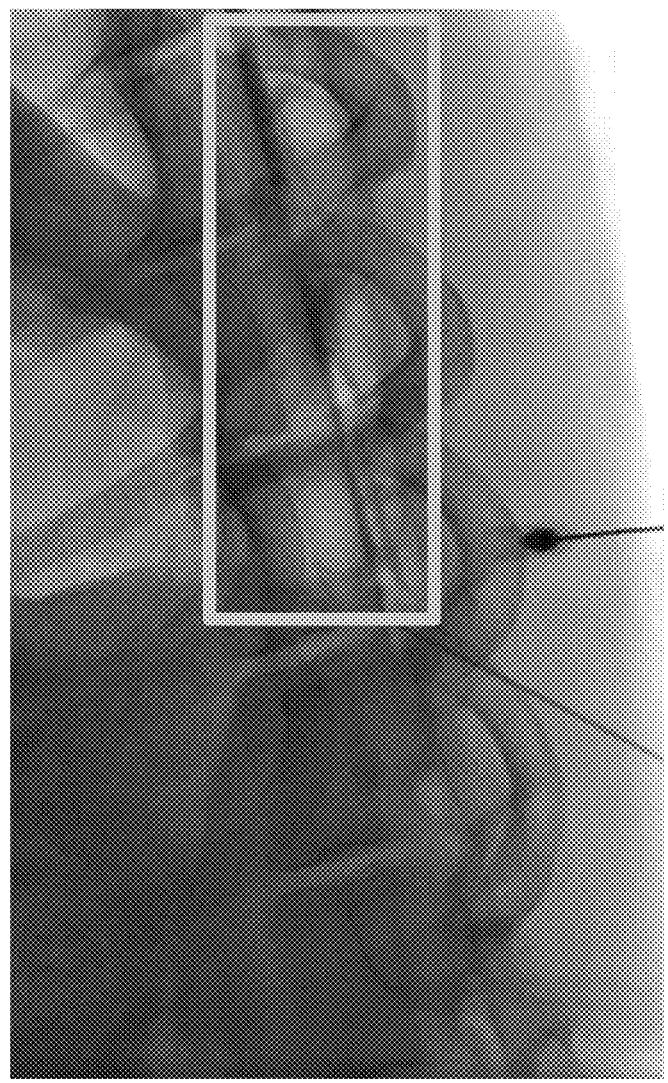
FIG. 10A and FIG. 10B show an image of animal #2 recorded 60 minutes post-injection with formulations SP-102 with 1.0% HA (FIG. 10A) and SP-102 with 1.25% HA (FIG. 10B).
Figure 10B:
Figure 11A:
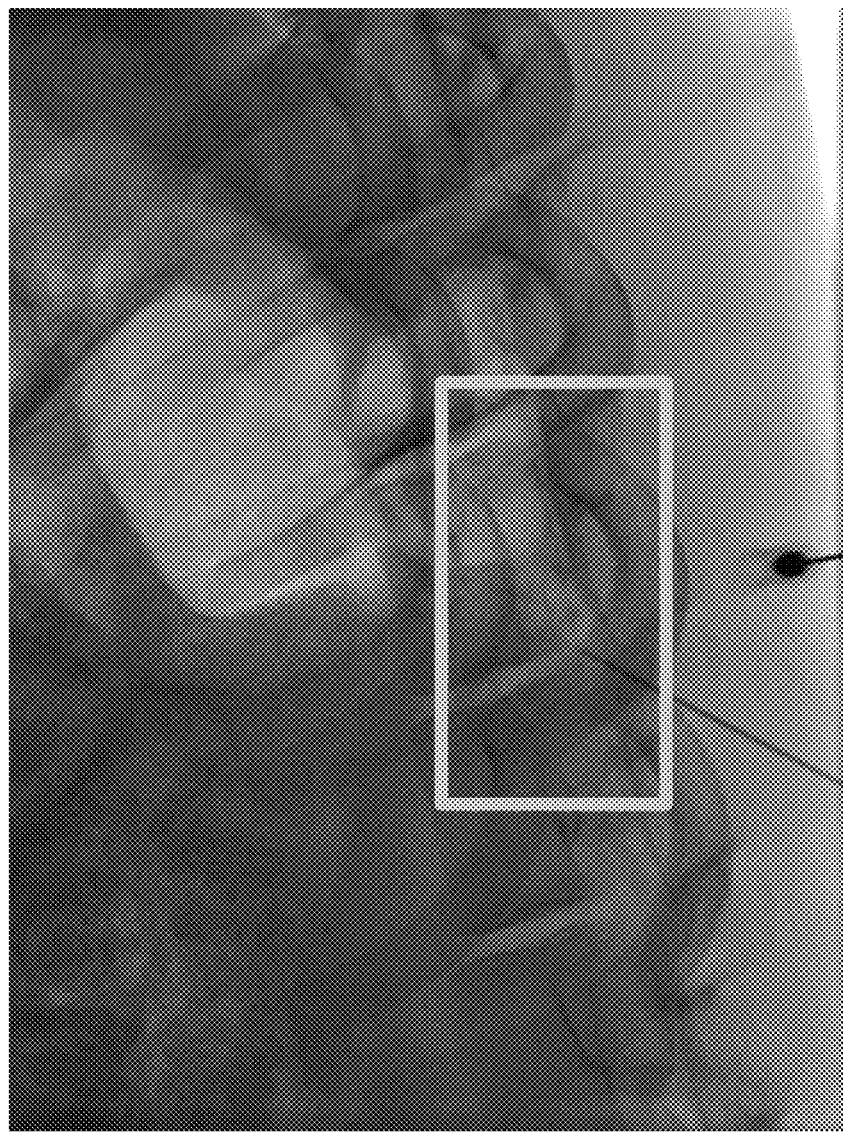
FIG. 11A and FIG. 11B show the images of animal #2 recorded 120 minutes post-injection with formulations SP-102 with 1.0% HA (FIG. 11A) and SP-102 with 1.25% HA (FIG. 11B).
Figure 11B:
Figure 12:
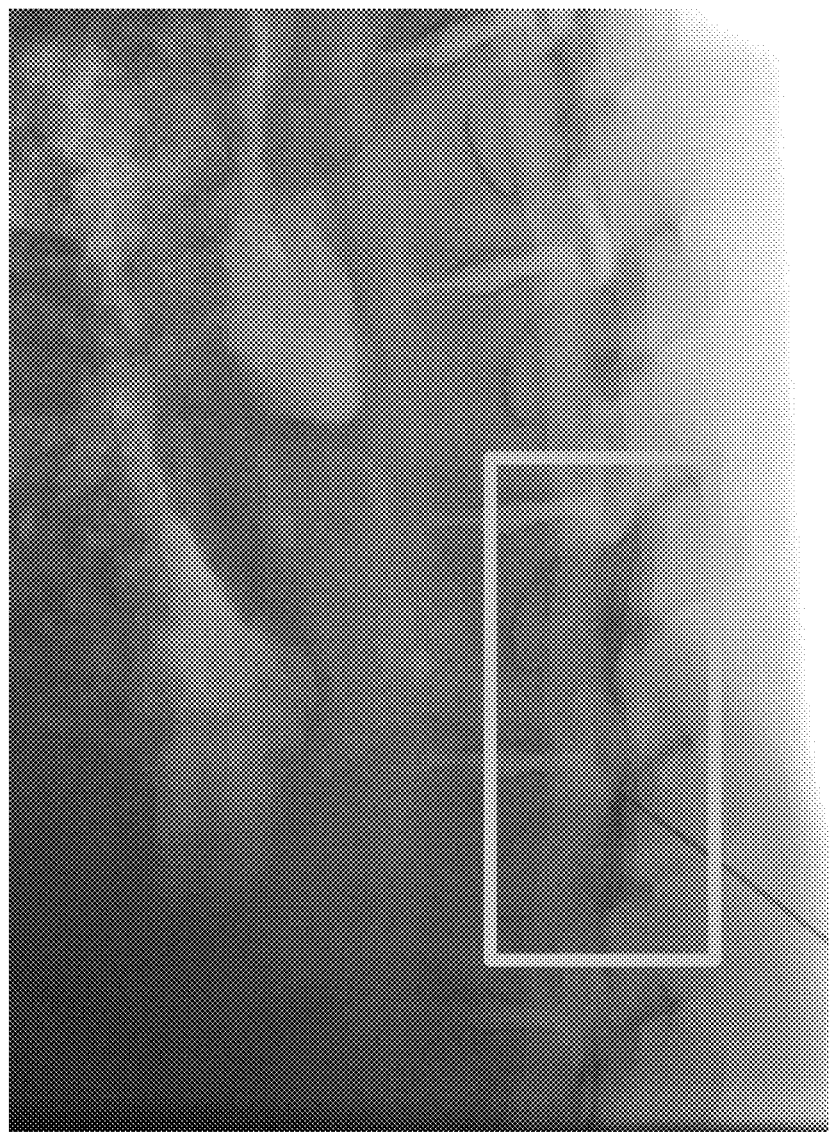
FIG. 12 shows the image recorded 180 minutes post-injection in animal #2 injected with formulation SP-102 (1.25% HA).

The post-injection images, recorded immediately following injection, are shown in FIGS. 8A-8B for the formulations SP-102 (1.0% HA) and SP-102 (1.25% HA). The corresponding images, recorded 30 min, 60 min, and 120 min after injection, are presented in FIGS. 9A-9B, FIGS. 10A-10B, and FIGS. 11A-11B, respectively. Lastly, the image recorded 180 min post-injection for formulation SP-102 (1.25% HA) is shown in FIG. 12.

The epidural injection time course studies show that SP-102 (1.25% HA) is localized to the injection site for a significantly longer period of time than commercial products.

Figure 13:
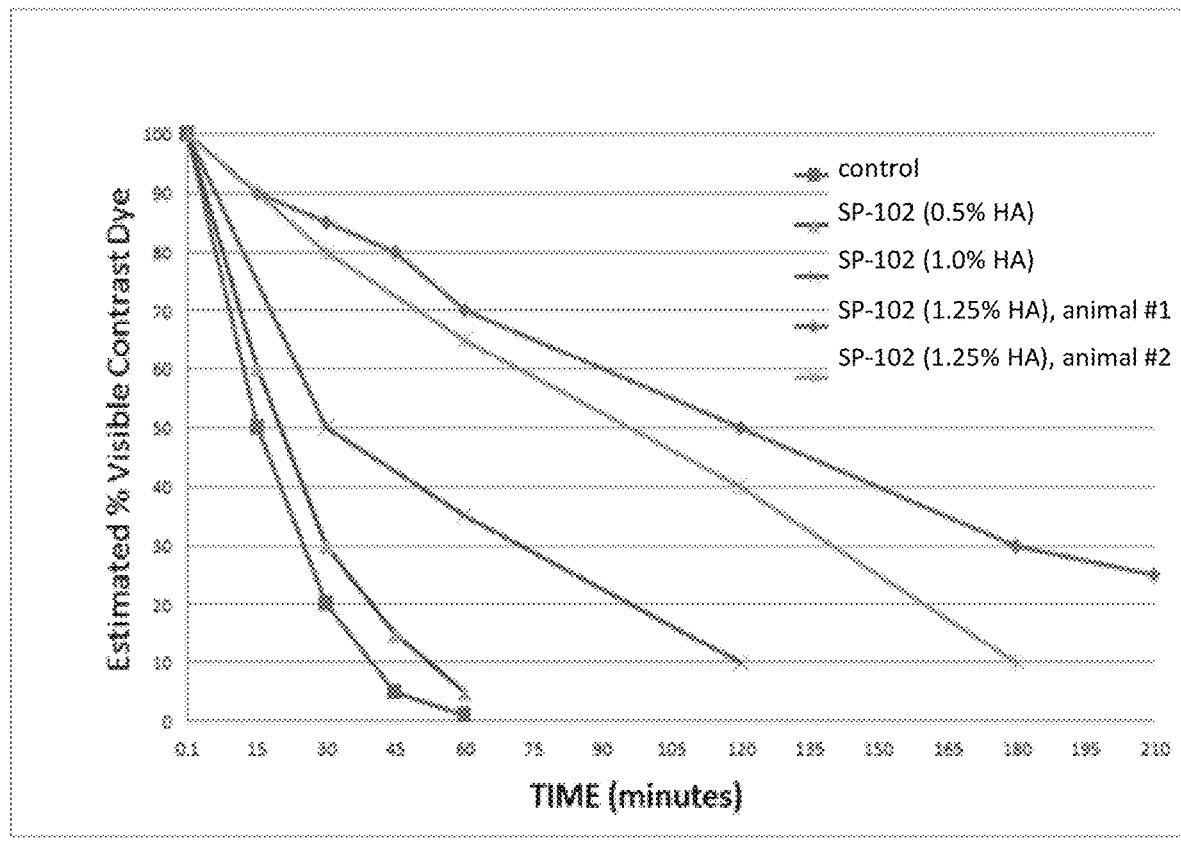
FIG. 13 shows a plot of the estimated percentage of visible contrast dye as a function of time for formulations SP-102 (0.5% HA), SP-102 (1.0% HA), and SP-102 (1.25% HA).
Figure 14:
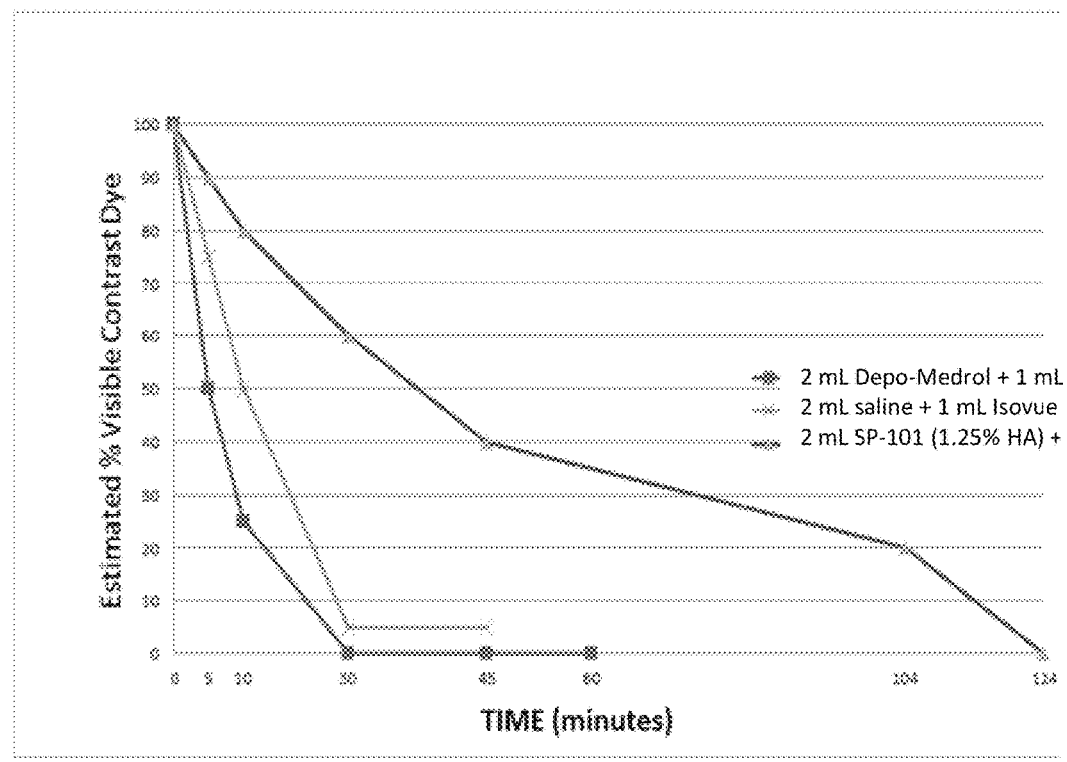
FIG. 14 shows a plot of the estimated percentage of visible contrast dye as a function of time for commercial injectable steroid products.

The post-injection images of the two animals are depicted graphically by tracking the estimated percentage of visible contrast dye as a function of time (FIG. 13). It is clear that addition of sodium hyaluronate results in prolongation of the residency time of dexamethasone in a dose-dependent manner. The epidural residency half-life of SP-102 (1.25% HA) is approximately 110 min. In contrast, the epidural residency half-life of commercial injectable steroid products (such as DEPO-MEDROL® and DECADRON®) is approximately 15 min (FIG. 14).

Example 6. Histopathological Study of SP-102 Formulations

Injections of commercial dexamethasone and SP-102 (1.25% HA) from Example 4 were analyzed by gross pathology and by histopathology. Briefly, the necropsy included examination of the external surface of the body, all orifices, and the thoracic and abdominal cavities, including their contents. Gross examination of the brain was also performed. The brain was collected and immersed in 10% NBF (neutral buffered formalin) for at least 24 hours. Subsequently, sections were cut at 4 µm, stained with Hematoxylin and Eosin (H&E), and examined using light microscopy. Observations of hemorrhage and/or necrosis/infarction are summarized in Table 9. The pathology data shows that there is no sign of infection or hemorrhage following injection of either commercial dexamethasone or SP-102 (1.25% HA).

TABLE 9

Histopathology of commercial dexamethasone and SP-102 (1.25% HA).

| Animal # | Slide # | Hemorrhage* | Necrosis/infarction* |
|---|---|---|---|
| 1 | 1 | 0 | 0 |
| 1 | 2 | 0 | 0 |
| 1 | 3 | 0 | 0 |
| 1 | 4 | 0 | 0 |
| 1 | 5 | 0 | 0 |
| 1 | 6 | 0 | 0 |
| 1 | 7 | 0 | 0 |
| 1 | 8 | 0 | 0 |
| 1 | 9 | 0 | 0 |
| 1 | 10 | 0 | 0 |
| 1 | 11 | 0 | 0 |
| 1 | 12 | 0 | 0 |
| 1 | 13 | 0 | 0 |
| 1 | 14 | 0 | 0 |
| 1 | 15 | 0 | 0 |
| 1 | 16 | 0 | 0 |
| 1 | 17 | 0 | 0 |
| 1 | 18 | 0 | 0 |
| 2 | 1 | 0 | 0 |
| 2 | 2 | 0 | 0 |
| 2 | 3 | 0 | 0 |
| 2 | 4 | 0 | 0 |
| 2 | 5 | 0 | 0 |
| 2 | 6 | 0 | 0 |
| 2 | 7 | 0 | 0 |
| 2 | 8 | 0 | 0 |
| 2 | 9 | 0 | 0 |
| 2 | 10 | 0 | 0 |
| 2 | 11 | 0 | 0 |
| 2 | 12 | 0 | 0 |
| 2 | 13 | 0 | 0 |
| 2 | 14 | 0 | 0 |
| 2 | 15 | 0 | 0 |
| 2 | 16 | 0 | 0 |
| 2 | 17 | 0 | 0 |
| 2 | 18 | 0 | 0 |

*scoring: 0, absent; 1, minimal; 2, mild; 3, moderate; 4, severe

The invention claimed is:

1. A method for treating pain in an individual in need thereof, comprising:
   injecting an aqueous pharmaceutical composition into an intralesional or intra-articular space of the individual, wherein the aqueous pharmaceutical composition comprises:
   a soluble corticosteroid selected from the group consisting of soluble salts of dexamethasone, and at least one viscosity enhancing agent,
   wherein the at least one viscosity enhancing agent is sodium hyaluronate or hyaluronic acid, the molecular weight of the at least one viscosity enhancing agent is between 500 kDa and 3.0 MDa, and the concentration of the at least one viscosity enhancing agent is between 1.0% w/v and 1.5% w/v;
   and wherein the aqueous pharmaceutical composition does not comprise insoluble corticosteroids.

2. The method of claim 1, wherein the aqueous pharmaceutical composition comprises between about 2 mg and about 20 mg of the soluble corticosteroid per dose.

3. The method of claim 1, wherein the aqueous pharmaceutical composition comprises between about 5 mg and about 15 mg of the soluble corticosteroid per dose.

4. The method of claim 1, wherein the aqueous pharmaceutical composition comprises about 10 mg of the soluble corticosteroid per dose.

5. The method of claim 1, wherein the soluble corticosteroid is dexamethasone sodium phosphate.

6. The method of claim 1, wherein the aqueous pharmaceutical composition comprises dexamethasone sodium phosphate at a concentration of about 6.58 mg/mL.

7. The method of claim 1, wherein the aqueous pharmaceutical composition comprises the soluble corticosteroid at a weight equivalent to achieve a dexamethasone concentration of about 5 mg/mL.

8. The method of claim 1, wherein the at least one viscosity enhancing agent is sodium hyaluronate.

9. The method of claim 1, wherein the at least one viscosity enhancing agent is hyaluronic acid.

10. The method of claim 1, wherein the concentration of the at least one viscosity enhancing agent is about 1.25% w/v.

11. The method of claim 1, wherein the aqueous pharmaceutical composition further comprises a preservative and/or an anesthetic.

12. The method of claim 1, wherein the aqueous pharmaceutical composition is preservative-free.

13. The method of claim 1, wherein the molecular weight of the at least one viscosity enhancing agent is between about 500 kDa and about 2.0 MDa.

14. The method of claim 1, wherein the molecular weight of the at least one viscosity enhancing agent is between about 1.0 MDa and about 2.5 MDa.

15. The method of claim 1, wherein the molecular weight of the at least one viscosity enhancing agent is between about 1.0 MDa and about 2.0 MDa.

16. The method of claim 1, wherein the molecular weight of the at least one viscosity enhancing agent is between about 1.2 MDa and about 1.8 MDa.

17. The method of claim 1, wherein the aqueous pharmaceutical composition has a viscosity of between about 1 kcP and about 10 kcP.

18. The method of claim 1, wherein the aqueous pharmaceutical composition has a viscosity of between about 1 kcP and about 5 kcP.

19. The method of claim 1, wherein less than 20 N of force is used to inject the aqueous pharmaceutical composition.

20. The method of claim 1, wherein no more than 27 N of force is used to inject the aqueous pharmaceutical composition.

21. The method of claim 1, wherein the individual is injected with the aqueous pharmaceutical composition once every 1 to 12 weeks.

22. The method of claim 1, wherein the individual has one or more of rheumatoid arthritis, osteoarthritis, lower back pain, spinal stenosis, disc herniation, radiculitis, or chronic discogenic pain.

23. The method of claim 1, wherein the individual has one or more of rheumatoid arthritis or osteoarthritis.

24. The method of claim 1, wherein the individual has rheumatoid arthritis.

25. The method of claim 1, wherein the method comprises injecting the aqueous pharmaceutical composition into the intralesional space of the individual.

26. The method of claim 1, wherein the method comprises injecting the aqueous pharmaceutical composition into the intra-articular space of the individual.

27. The method of claim 1, wherein the method comprises a step of administering to the individual an anesthetic agent.

28. The method of claim 27, wherein the anesthetic agent is lidocaine, bupivacaine, or benzocaine.

29. The method of claim 27, wherein the anesthetic agent is administered separate to the aqueous pharmaceutical composition.

* * * * *